(12) United States Patent
Beaulieu et al.

(10) Patent No.: US 6,960,585 B2
(45) Date of Patent: Nov. 1, 2005

(54) AMINO-SUBSTITUTED TETRACYCLIC COMPOUNDS USEFUL AS ANTI-INFLAMMATORY AGENTS AND PHARMACEUTICAL COMPOSITIONS COMPRISING SAME

(75) Inventors: Francis Beaulieu, Laprairie (CA); Carl Ouellet, Boucherville (CA); Makonen Belema, New Haven, CT (US); Yuping Qiu, Windsor, CT (US); Xuejie Yang, Middletown, CT (US); Fred C. Zusi, Hamden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 612 days.

(21) Appl. No.: 09/965,977

(22) Filed: Sep. 27, 2001

(65) Prior Publication Data

US 2002/0072523 A1 Jun. 13, 2002

Related U.S. Application Data

(60) Provisional application No. 60/223,304, filed on Oct. 3, 2000.

(51) Int. Cl.$^7$ .................. A61K 31/519; A61K 31/4985; C07D 487/04
(52) U.S. Cl. ...................... 514/248; 514/257; 514/285; 514/287; 544/247; 544/343; 546/64
(58) Field of Search ................... 514/248, 257, 514/285, 287; 544/247, 343; 546/64

(56) References Cited

U.S. PATENT DOCUMENTS

| | | | |
|---|---|---|---|
| 4,160,097 A | 7/1979 | Warner, Jr. et al. | 548/346 |
| 4,225,724 A | 9/1980 | Warner, Jr. et al. | 548/346 |
| 4,236,015 A | 11/1980 | Warner, Jr. et al. | 548/346 |
| 5,153,196 A * | 10/1992 | McQuaid et al. | 514/250 |
| 5,182,386 A | 1/1993 | Albaugh et al. | 540/350 |
| 5,196,421 A | 3/1993 | McQuaid et al. | 514/250 |
| 5,266,575 A | 11/1993 | Gerster et al. | 514/293 |
| 5,990,109 A | 11/1999 | Chen et al. | 514/250 |
| 2003/0022898 A1 * | 1/2003 | Burke et al. | 514/250 |

FOREIGN PATENT DOCUMENTS

| | | |
|---|---|---|
| WO | WO 94/07893 | 4/1994 |
| WO | WO 97/19079 | 5/1997 |
| WO | 99/09845 | 3/1999 |

OTHER PUBLICATIONS

Ceccarelli et al., Eur. J. Med. Chem. 33 (1998) p. 943–955.

* cited by examiner

*Primary Examiner*—Richard L. Raymond
*Assistant Examiner*—Tamthom N. Truong
(74) *Attorney, Agent, or Firm*—Terence J. Bogie; Anastasia P. Winslow; Stephen B. Davis

(57) ABSTRACT

Compounds of formula (I), or pharmaceutically-acceptable salts thereof, are useful in treating inflammatory and immune diseases and disorders,

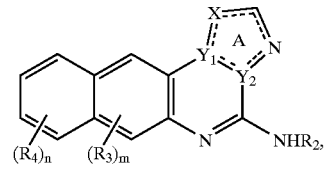

(I)

wherein X, $Y_1$, $Y_2$, and $R_{2-4}$ are as defined in the specification.

15 Claims, No Drawings

AMINO-SUBSTITUTED TETRACYCLIC COMPOUNDS USEFUL AS ANTI-INFLAMMATORY AGENTS AND PHARMACEUTICAL COMPOSITIONS COMPRISING SAME

RELATED INVENTIONS

This application claims the benefit of U.S. application Serial No. 60/223,304, filed Oct. 3, 2000, pursuant to 35 U.S.C. § 119(e).

FIELD OF THE INVENTION

The present invention relates to amino-substituted tetracyclic compounds, methods of using the compounds in treating inflammatory and immune diseases, and pharmaceutical compositions comprising the compounds.

BACKGROUND OF THE INVENTION

Tumor necrosis factor (TNF-α) is a potent cytokine having pro-inflammatory properties that is released by many cell types when stimulated. Studies have shown a relationship between elevated levels of TNF-α and a variety of diseases including septic shock, hematopoiesis, tumors, and inflammatory disorders of the central nervous system including HIV encephalitis, cerebral malaria, and meningitis. Neurodegenerative diseases such as Alzheimer's disease, Parkinson's disease, and Creutzfeldt-Jacob disease also are reportedly associated with enhanced TNF-α levels. See, e.g., Arvin et al., "*The Role of Inflammation and Cytokines in Brain Injury*," Neuroscience and Biobehavioral Reviews, Vol. 20, No. 3 (1996), at pp. 445–452. Accordingly, various classes of compounds have been researched and developed to inhibit TNF-α production at both transcriptional and translational levels, e.g., corticosteroids, rolipram (a phosphodiesterase IV inhibitor suppressing TNF-αmRNA synthesis), calphostin, and imidazole-type cytokine suppressing anti-inflammatory drugs (CSAIDs). See, e.g., Dinarello, "*Role of Pro- and Anti-Inflammatory Cytokines During Inflammation: Experimental and Clinical Findings*," Review, Vol. 0393–974X (1997), at pp. 91–103.

Recently, attention has focussed on the role of Nuclear factor-κB (NF-κB) in the activation pathway that leads to production of TNF-α and other inflammatory cytokines and gene types. Besides TNF-α, NF-κB modulates many genes involved in immune function and inflammation, including IL-2, IL-6, IL-8, IL-2Rα, GM-GSF, intercellular adhesion molecule (ICAM-1), and vascular cellular adhesion molecule-1 (VCAM-1). Thus, inhibition of NF-κB and/or its activation pathway provides a means for treating a wide range of diseases including autoimmune diseases, Alzheimer's disease, atherosclerosis, oncogenesis, and so forth. See, e.g., Baldwin, "*The NF-κB and IκB Proteins: New Discoveries and Insights*," Annual Rev. Immunol. Vol. 14 (1996), at pp. 649–81; see also Christman et al., "*Impact of Basic Research on Tomorrow's Medicine, The Role of Nuclear Factor-κB in Pulmonary Diseases*," Chest, Vol. 117 (2000), at pp. 1482–87.

Potential inhibitors of NF-κB and/or the NF-κB pathway have been identified as including Interleukin-10, glucocorticoids, salicylates, nitric oxide, and other immunosuppressants. IκB is a cytoplasmic protein that controls NF-κB activity by retaining NF-κB in the cytoplasm. IκB is phosphorylated by the IκB kinase (IKK), which has two isoforms, IKK-α (or "IKK-1") and IKK-β (or "IKK-2"). Upon phosphorylation of IκB by IKK, NF-κB is rapidly released into the cell and translocates to the nucleus where it binds to the promoters of many genes and up-regulates the transcription of pro-inflammatory genes. Glucocorticoids reportedly inhibit NF-κB activity by two mechanisms, i.e., upregulating IκB protein levels and inhibiting NF-κB subunits. Nitric oxide also reportedly inhibits NF-κB through upregulation of IκB. However, these mechanisms of interaction are complex; for example, production of nitric oxide in lymphocytes reportedly enhances NF-κB activity.

As may be appreciated, those in the field of pharmaceutical research continue to seek to develop new compounds and compositions having increased effectiveness, bioavailability, and solubility, having fewer side effects, and/or providing the consumer with a choice of options. Particularly in the area of immune response, many individuals respond differently depending upon the type of treatment and chemical agent used. Mechanisms of action continue to be studied to aid in understanding the immune response and in developing compounds effective for treating immune-related disorders.

The present invention provides 4-amino substituted benzoquinoline, benzoquinoxaline, and benzoquinazoline compounds having five-membered heterocycles (e.g., pyrazolyl, imidazolyl, and thiazolyl rings) fused thereto. The compounds are useful as anti-inflammatory agents and/or for treating conditions associated with TNF-α and NF-κB.

Lactam-based tetracyclic compounds useful as antagonists of NMDA (N-methyl-D-aspartate) and AMPA (α-3-hydroxy-5-methylisoxazole-4-propionate) receptors are disclosed in WO 94/07893, Preparation of 5H, 10H-imidazo [1,2-a]indeno[1,2-e]pyrazine-4-one AMPA/KA Receptor Antagonist, filed by Aloup et al; and in articles by Mignani, Aloup, et al., "*Synthesis and Pharmacological Properties of 5H, 10H-imidazo[1,2-a]indeno[1,2-e]pyrazine-4-one, a New Competitive AMPA/KA Receptor Antagonist*," Drug. Dev. Res., Vol. 48 (3) (1999), at pp. 121–29, and "*An Efficient Preparative Route to Fused Imidazo[1,2-a]-Pyrazin-4-one Derivatives*," Heterocycles, Vol. 50, No. 1 (1999), at pp. 259–267. Compounds such as lactams that are claimed to be useful for blocking excitatory amino acid receptors found in the brain and spinal cord are shown in U.S. Pat. Nos. 5,153,196 and 5,196,421, both assigned to Eli Lilly and Company. Tricyclic compounds having amino-substituents claimed to be useful as brain receptor ligands are disclosed in U.S. Pat. No. 5,182,386, assigned to Neurogen Corp., and in U.S. Pat. Nos. 4,160,097, 4,172,947, 4,191,766, 4,191,767, 4,198,508, 4,200,750, 4,225,724, and 4,236,015, in WO97/19,079, and in S. Ceccarelli et al, "*Imidazo[1,2-a]quinoxalin-4-amines: A Novel Class of Non-xanthine $A_1$-Adenosine Receptor Antagonists*," European Journal of Medicinal Chemistry Vol. 33, (1998), at pp. 943–955. To applicants' knowledge, 4-amino substituted tetracyclic compounds according to formula (I) have not been previously described.

The patents and articles cited above are incorporated herein by reference.

SUMMARY OF THE INVENTION

The invention is directed to a compound of the formula (I), useful in treating inflammatory or immune diseases or disorders:

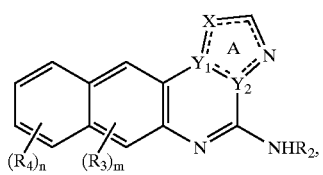

(I)

or a pharmaceutically-acceptable salt thereof, wherein
X is $NR_1$, $CR_1$, or S;
$Y_1$ and $Y_2$ are nitrogen or carbon, provided that
a) when X is $CR_1$, at least one of $Y_1$ and $Y_2$ is nitrogen, and b) when one of $Y_1$ and $Y_2$ is carbon, the other of $Y_1$ and $Y_2$ is nitrogen and/or X is $NR_1$ or S, so that ring A defines a five-membered heteroaryl ring having at least two heteroatoms;
$R_1$ is hydrogen, halogen, alkyl, substituted alkyl, cyano, $OR_5$, $NR_5R_6$, $C(=O)R_5$, $CO_2R_5$, or aryl;
$R_2$ is alkyl, substituted alkyl, alkenyl, alkynyl, alkoxy, alkylthio, aryl, heteroaryl, heterocyclo, cycloalkyl, or substituted cycloalkyl;
$R_3$ and $R_4$ are independently selected from halogen, alkyl, substituted alkyl, nitro, cyano, $OR_7$, $NR_7R_8$, $C(=O)R_7$, $CO_2R_7$, $C(=O)NR_7R_8$, $NR_7C(=O)R_8$, $NR_7C(=O)OR_8$, $S(O)_qR_7$, $NR_7SO_2R_8$, and $SO_2NR_7R_8$;
$R_5$, $R_6$, $R_7$, and $R_8$ are independently selected from hydrogen, alkyl, substituted alkyl, and phenyl, or when attached to the same nitrogen atom (as in $NR_5R_6$ or $NR_7R_8$) may join together to form a heterocycle or heteroaryl;
m, n and q are independently 0, 1, or 2.

Advantageously, $R_2$ is an alkyl optionally substituted with OR' or NR'R", as defined in the specification. The invention also relates to pharmaceutical compositions containing at least one compound of formula (I) and a pharmaceutically-acceptable carrier or diluent. Also included within the invention are methods of treating inflammatory and immune diseases and disorders comprising administering to a mammal in need of such treatment an effective amount of at least one compound of formula (I).

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth.

The term "substituted alkyl" refers to an alkyl group as defined above having one, two, or three substituents selected from the group consisting of halo, amino, cyano, hydroxy, alkoxy, alkylthio, —C(=O)H, —CO$_2$H, —(C=O)alkyl, —CO$_2$alkyl, cycloalkyl, substituted cycloalkyl, aryl, heteroaryl, or heterocycle. Thus, the term "substituted alkyl" includes a polyfluoroalkyl, i.e., where two or more hydrogen atoms of an alkyl chain are replaced by a fluorine atom, such as with trifluoromethyl. The term "substituted alkyl" also includes an alkyl group as defined above having the substituent NR'R", wherein each of R' and R" are independently selected from the group consisting of hydrogen, alkyl, substituted alkyl, hydroxy, alkoxy, —C(=O)H, —CO$_2$H—(C=O)alkyl, —CO$_2$-alkyl, cycloalkyl, substituted cycloalkyl, aryl, heteroaryl, and heterocycle. Alternatively, R' and R" may together form a heterocyclo or heteroaryl ring. A substituted lower alkyl or substituted $C_{1-4}$alkyl refers to an alkyl group of 1–4 carbon atoms having one to three substituents selected from those recited above for alkyl groups generally.

The term "alkoxy" refers to an alkyl group as defined above bonded through an oxygen atom (—O—), and the term "alkylthio" refers to an alkyl group as defined above bonded through a sulfur atom (—S—). For example, such groups include methoxy, methylthio, ethoxy, ethylthio, n-propoxy, n-propylthio, isopropoxy, isopropylthio, n-butoxy, n-butylthio, tert-butoxy, tert-butylthio, n-pentoxy, n-pentylthio, and so forth.

The term "alkenyl" refers to straight or branched chain hydrocarbon groups having 2 to 12 carbon atoms and at least one double bond. Alkenyl groups having 2 to 6 carbon atoms and one double bond are most preferred. Exemplary alkenyl groups include ethenyl, 1-methyl-ethenyl, 1- or 2-propenyl, 1-methyl-1-propenyl, 1-methyl-2-propenyl, 1,1-dimethyl-2-propenyl, 2-methyl-2-propenyl, 1-, 2- or 3-butenyl, 1-methyl-1-butenyl, 2-methyl-1-butenyl, 3-methyl-1-butenyl, 3,3-dimethyl-1-butenyl, 2, 3-dimethyl-1-butenyl, 1-methyl-2-butenyl, 1,1-dimethyl-2-butenyl, 2-methyl-2-butenyl, 3-methyl-2-butenyl, 1,3-butadienyl, 1,3-dimethyl-1,3-butadienyl, 1-, 2-, 3- or 4-pentenyl, and so forth.

The term "alkynyl" refers to straight or branched chain hydrocarbon groups having 2 to 12 carbon atoms and at least one triple bond. Alkynyl groups of 2 to 6 carbon atoms and having one triple bond are most preferred. Exemplary alkynyl groups include ethynyl, 1- or 2-propynyl, 1-methyl-2-propynyl, 1,1-dimethyl-2-propynyl, 1-, 2- or 3-butynyl, 3-methyl-1-butynyl, 3,3-dimethyl-1-1s butynyl, 1-methyl-2-butynyl, 1,1-dimethyl-2-butynyl, 1-, 2-3, or 4-pentynyl, and so forth.

The term "amino" when used alone refers to $NH_2$. When used to define a substituent, as in 4-amino substituted tetracycles, the term "amino" refers to the group NR'R", wherein R' and R" are as defined above for alkyl.

The term "carbonyl" refers to —C(=O)—, and "carboxy" refers to —CO$_2$—. Thus, carbonyl$C_{1-4}$alkyl refers to the group —C(=O) linked to a $C_{1-4}$alkyl.

The term "halo" or "halogen" refers to chloro, bromo, fluoro and iodo.

The term "cycloalkyl" refers to fully saturated and partially unsaturated hydrocarbon rings of 3 to 9, preferably 3 to 7, carbon atoms as well as such rings having a fused aryl ring such as indan or a bridge of three to four carbon atoms as in bicycloheptane.

The term "substituted cycloalkyl" refers to such rings having one, two, or three substituents, preferably one, selected from the group consisting of alkyl, substituted alkyl, alkoxy, alkylthio, halo, hydroxy, cyano, amino, —NH(alkyl), —NH(cycloalkyl), —N(alkyl)$_2$, —CO$_2$H, —CO$_2$lower alkyl, aryl, heterocyclo, heteroaryl, keto (=O), =N—OH, =N—O-lower alkyl, and a five or six membered ketal, i.e., 1,3-dioxolane or 1,3-dioxane.

The term "aryl" refers to phenyl, 1-naphthyl and 2-naphthyl, with phenyl being preferred. When the term "aryl" is used, it encompasses such rings having from zero, one, two or three substituents selected from the group consisting of alkyl, substituted alkyl, alkoxy, alkylthio, halo, hydroxy, nitro, cyano, amino, —NH(alkyl), —NH(cycloalkyl), —N(alkyl)$_2$, —CO$_2$H, —(C=O)alkyl, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, phenyl, benzyl, phenylethyl, phenyloxy, phenylthio, heterocyclo, and heteroaryl.

The term "heterocyclo" or "heterocycle" refers to substituted and unsubstituted non-aromatic 3 to 7 membered monocyclic groups, 7 to 11 membered bicyclic groups, and 10 to 15 membered tricyclic groups which have at least one heteroatom (O, S or N) in at least one of the rings. When the heterocyclo is monocyclic, five- or six-membered rings are preferred; when bicyclic, fused 5,6- or 6,6-membered ring systems are preferred; and when tricyclic, ring systems having one five and two six membered rings, or three six membered rings, are preferred. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom.

Whenever the term "heterocyclo" or "heterocycle" is used, any ring of the heterocyclo group may optionally contain one, two, or three substituents selected from the group consisting of halo, amino, cyano, alkyl, substituted alkyl, —NH(alkyl), —NH(cycloalkyl), —N(alkyl)$_2$, alkoxy, alkylthio, hydroxy, nitro, phenyl, benzyl, phenylethyl, phenyloxy, phenylthio, —CO$_2$H, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, heterocyclo, heteroaryl, keto, =N—OH, =N—O—lower alkyl, and a five or six membered ketal, i.e., 1,3-dioxolane or 1,3-dioxane.

Exemplary monocyclic groups include tetrahydrothienyl, tetrahydrofuryl, azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. When the heteroaryl is monocyclic, five- or six membered rings are preferred; when bicyclic, fused 5,6- or 6,6-membered ring systems are preferred; and when tricyclic, ring systems having one five and two six membered rings, or three six-membered rings, are preferred. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic include at least one fully aromatic ring but the other fused ring or rings may be aromatic or non-aromatic. The heteroaryl group may be attached at any available nitrogen or carbon atom of any ring.

Whenever the term "heteroaryl" is used herein, any ring of the heteroaryl group may optionally contain one, two or three substituents selected from the group consisting of halo, amino, cyano, alkyl, substituted alkyl, —NH(alkyl), —NH(cycloalkyl), —N(alkyl)$_2$, alkoxy, alkylthio, hydroxy, nitro, phenyl, benzyl, phenylethyl, phenyloxy, phenylthio, —CO$_2$H, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, heterocyclo, and heteroaryl.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, triazolyl, and the like.

Exemplary bicyclic heteroaryl groups include indolyl, isoindolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, benzopyranyl, cinnolinyl, quinoxalinyl, quinazolinyl, indazolyl, pyrrolopyridyl, furopyridinyl, dihydroisoindolyl, tetrahydroquinolinyl, napthyridinyl, pteridinyl, and the like.

Exemplary tricyclic heteroaryl groups include carbazolyl, benzidolyl, phenanthrollinyl, acridinyl, phenanthridinyl, xanthenyl and the like.

When reference is made herein to a bond having a solid and dashed line, such as in

, it should be understood that the bond(s) may be selected from a single or a double bond, as appropriate, given selections for adjacent atoms. For example, when there is shown

if X is sulfur or NH, the bonds linking X to adjacent atoms A and B are single bonds. However, when in

X is CR$_1$ or a nitrogen atom, one of the bonds linking X to A or B is a double bond and the other is a single bond.

Throughout the specification, groups and substituents thereof may be chosen by one skilled in the field to provide stable moieties and compounds.

The compounds of formula I form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula I contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as TEA, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Sodium or potassium salts are preferred.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. For example, compounds containing a carboxy group can form physiologically hydrolyzable esters which serve as prodrugs by being hydrolyzed in the body to yield formula I–II compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis (E and Z) isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended.

Methods of Preparation

The inventive compounds may be prepared by methods such as those illustrated in the following Schemes I to V. Starting materials are commercially available or can be readily prepared by one of ordinary skill in the art, and/or modifications can be made to the methods of Schemes I to V by one skilled in the art, using known methods. For all of the schemes and compounds, the groups $R_1$, $R_2$, $R_3$ and $R_4$ are as described herein for a compound of formula I, unless otherwise indicated, and appropriate starting materials may be selected by one skilled in the field having the desired groups $R_1$, $R_2$, $R_3$ and $R_4$. Groups designated R', as well as solvents, temperatures, pressures, and other reaction conditions, may be selected by one of ordinary skill in the art. For example, in these schemes chlorinating agents may include phosphorous oxychloride, catalytic agents may include metals such as Pd, and solvents may be selected from 1,2-dichlorobenzene, methylene chloride, DMF, THF, alcohols, ethers, dioxane, acetonitrile, water, mixtures of ethers and water, and the like.

Abbreviations

For ease of reference the following abbreviations are used in the schemes and Examples herein:
Me=methyl
Et=ethyl
MeOH=methanol
EtOH=ethanol
i-PrOH=isopropanol
Ph=phenyl
Bz=benzyl
DCM=dichloromethane
DMF=dimethyl formamide
DMSO=dimethyl sulfoxide NaOH=sodium hydroxide
TEA or Et$_3$N=triethylamine
TFA=trifluoroacetic acid
THF=tetrahydrofuran
K$_2$CO$_3$=potassium carbonate
Na$_2$S$_2$O$_3$=sodium thiosulfate
min=minute(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS=mass spectrometry
NMR=nuclear magnetic resonance
mp=melting point Definitions of Terms Used in the Reaction Schemes The following are definitions of terms used herein and in the reaction schemes.

"Acetal, ketal, thioacetal or thioketal formation" are processes known in the art and illustrated in "Protective Groups in Organic Synthesis", Second Ed., T. W. Green and P. G. W. Wuts, John Wiley & Sons, New York, 1991, Chapter 4 and references therein, incorporated herein by reference.

"Acid halide formation" includes methods of converting a carboxylic acid to an acid halide. For example, this reaction may be performed with thionyl chloride, oxalyl chloride or bromide in the presence of DMF in DCM and phosphorus trichloride or tribromide.

"Alkylation" includes all alkylation procedures such as alkylation of desired alcohol or ketone groups by treatment with organic or inorganic base in an appropriate organic solvent, followed by addition of an alkylating agent such as an alkyl, allyl or benzyl halide, mesylate or tosylate to the generated enolate, phenolate or thiophenolate.

"Aromatic substitution" includes all aromatic substitution methods known in the field including nucleophilic substitutions of aromatic halides by water in presence of sulfuric acid or trifluoroacetic acid, or by alkoxides, aryloxides, thioalkoxides or thioaryloxides in an inert organic solvent. Copper salts may be used to promote the reaction of aryl halides with alkoxides, and Pd(0) salts may be used to promote the reaction with thioalkoxides.

"Aromatic halogenation" includes the addition of chlorine, bromine or iodine to an aromatic ring optionally with a catalyst, e.g. iron or a Lewis acid. It also includes the reaction of N-chloro and N-bromoamides catalyzed by the addition of acids. For iodination, iodine may be used with copper salts, silver trifluoromethanesulfonate, thallium(I) acetate, or with an oxidizing agent such as nitric acid, iodic acid, sulfur trioxide or hydrogen peroxide. Iodine monochloride can also be used.

"Cross-coupling" includes all cross-coupling methods known by those skilled in the art. Such methods include the reaction of a vinyl or aromatic triflate, bromide or iodide with a tin (Stille-type), zinc, magnesium or boronate (Suzuki-type) derivative catalyzed by a palladium(0), palladium(II), nickel(0) or nickel(II) catalyst. Copper iodide, lithium chloride, zinc chloride or triphenylarsine, tris(2-furyl)phosphine or tris(2,4,6-trimethoxyphenyl)phosphine advantageously may also be added. When a boronic acid derivative is used, the reaction proceeds in the presence of an inorganic base such as potassium phosphate or carbonate or sodium carbonate. The cross-coupling reactions are performed in an inert organic solvent.

"Grignard type reaction" includes the addition of an organometallic compound to a carbonyl-containing compound. This includes addition of Grignard reagents, alkyl or aryllithiums, alkylzinc, alkylaluminum, organotitanium, organozirconium or organocerium compounds in an inert organic solvent such as ethyl ether, THF, DCM, benzene, toluene, or the like. Complexing of the ketone or the Grignard reagent with cerium halides, perchlorate salts or tetraalkylammonium halides may sometimes be advantageous to improve the addition reaction. The term "Grignard type reaction" is also intended to include the addition of a Grignard reagent to an acid chloride that has been first reacted with tributylphosphine to form the corresponding phosphonium salt. The reaction is performed in an inert organic solvent.

"Hydrolysis" includes the hydrolysis of esters and carbonyl protecting groups. For example, methyl or ethyl esters may be removed with aqueous solutions of sodium or potassium alkoxides in THF or EtOH. The hydrolysis of tert-butyl esters advantageously is carried out under acidic conditions such as 90% trifluoroacetic acid or 6N hydrochloric acid in solvents such as THF or DCM. Allyl esters may be removed with Pd(0) catalyst in an organic solvent. Silyl esters such as trimethylsilylethyl esters may be cleaved with tetrabutylammonium fluoride in THF. The hydrolysis of ketals and acetals may be carried out under acidic conditions such as IN hydrochloric acid, 80% acetic acid or p-toluenesulfonic acid in solvents such as THF or acetone.

"Imine formation" procedures are known in the field. For example, a ketone may be reacted with an amine in presence of an acid with or without a drying agent. Various inorganic and organic acids may be used, such as zinc chloride, titanium chloride, hydrochloric acid, sulfuric acid, trifluoroacetic acid, acetic acid, p-toluenesulfonic acid and the like, in solvents such as DCM, EtOH, benzene, toluene, THF, DMF and the like.

Scheme I
Benzo-imidazo-quinoxalines

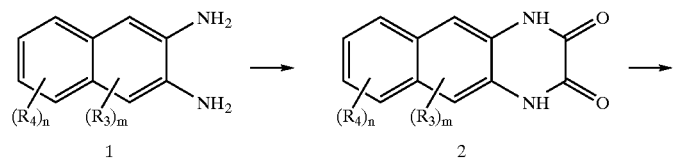

-continued

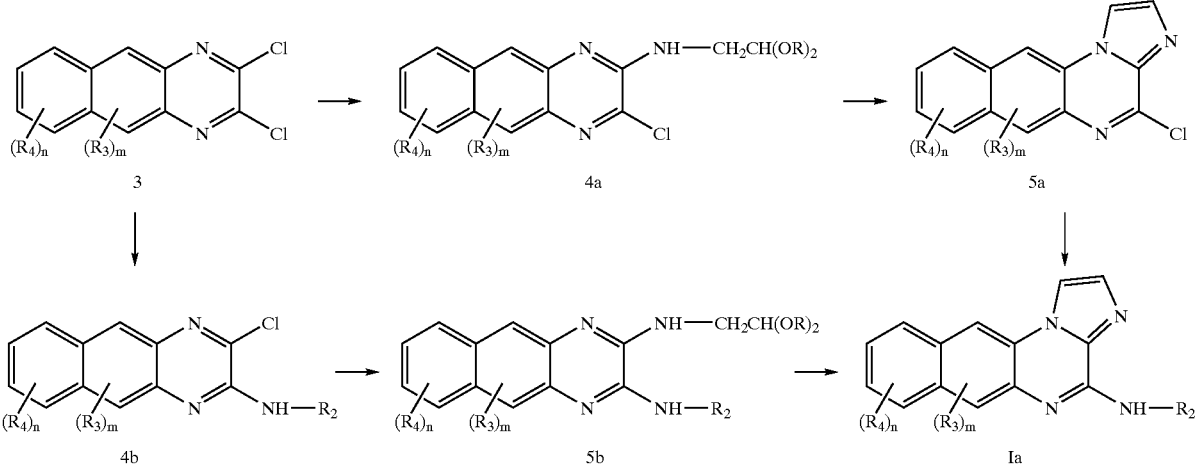

Benzo-imidazo-quinoxalines of formula Ia (wherein $Y_1$ of formula I is N, X is $CR_1$ and $R_1$ is hydrogen) may be prepared as above. Substituted 2,3-diaminonaphthalenes 1 are reacted with, for example, diethyl oxalate or oxalyl chloride to give annulated quinoxalinediones 2. Diones 2 are reacted with a chlorinating agent to give dichlorides 3. Dichlorides 3 are reacted with amine reagents comprising aminoacetaldehyde acetal and an appropriate primary amine ($R_2$-$NH_2$), and cyclized, wherein the order of reactivity may be adjusted depending upon chlorine atom reactivity.

For example, dichlorides 3 may first be reacted with an aminoacetaldehyde acetal to give amino-chloro derivatives 4a. The amino-chloro derivatives 4a may be cyclized to give the chloro-benzo-imidazoquinoxaline 5a, which may, in turn, be reacted with various primary amines ($R_2$—$NH_2$) to give compounds of formula (Ia).

Alternatively, where the undesired chlorine atom has greater reactivity (e.g., due to substituents $R_3$ and $R_4$), the order of addition of the amine reagents can be reversed, as shown for structures 4b and 5b. Dichloride 3 is reacted with primary amines ($R_2$—$NH_2$) to give amino-chloro derivatives 4b, which are then reacted with an aminoacetaldehyde acetal to give diamino compounds 5b, which are then cyclized to give the compound of formula Ia.

Exemplary aminoacetaldehyde acetals comprise aminoacetaldehyde, dimethyl acetal, or aminoacetaldehyde, diethyl acetal. Cyclization is typically performed under acidic conditions.

Scheme II
Substituted benzo-imidazo-quinoxalines

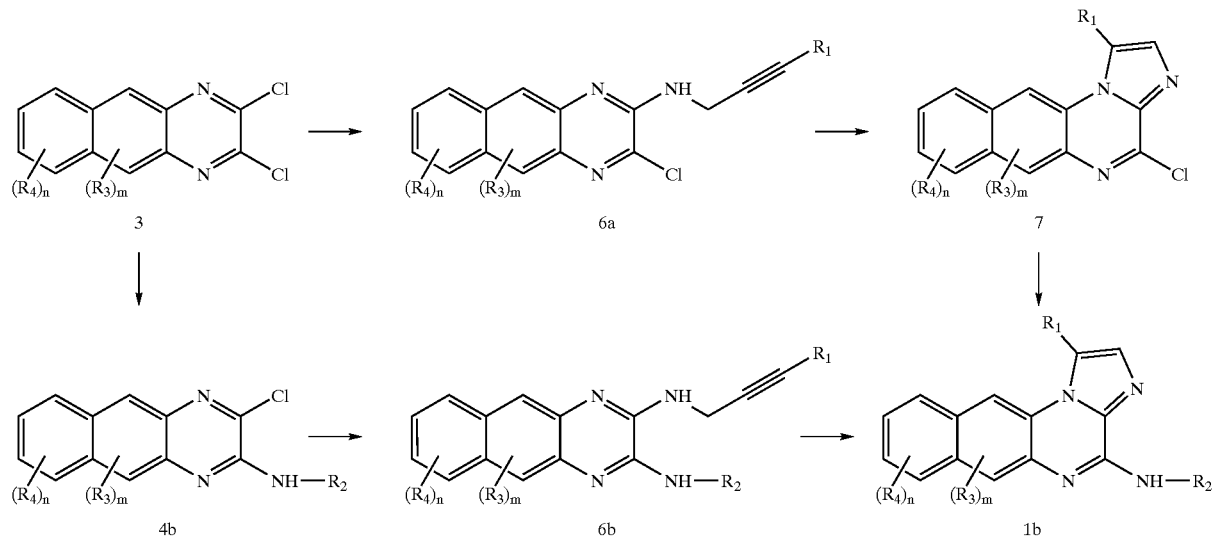

1-Substituted benzo-imidazo(1,2-a)quinoxalines of formula Ib (wherein $Y_1$ of formula I is N, X is $CR_1$ and $R_1$ is substituted lower alkyl) may be prepared as shown in Scheme II. Dichloro compounds 3 are prepared as shown in Scheme I and reacted with substituted propargylamines ($R_1$—C≡C—$CH_2$—$NH_2$) to give amino-chloro derivatives 6a, which are cyclized to 1-substituted chloro-benzo-imidazoquinoxalines 7. Suitable primary amines are reacted with 7 to give compounds of formula Ib.

Alternatively, the order of reactivity may be adjusted, wherein dichloro compounds 3 are first reacted with suitable primary amines to give derivatives 4b, as in Scheme I, and then reacted with propargyl amines to amino derivatives 6b, which may be cyclized as above to give compounds of formula Ib.

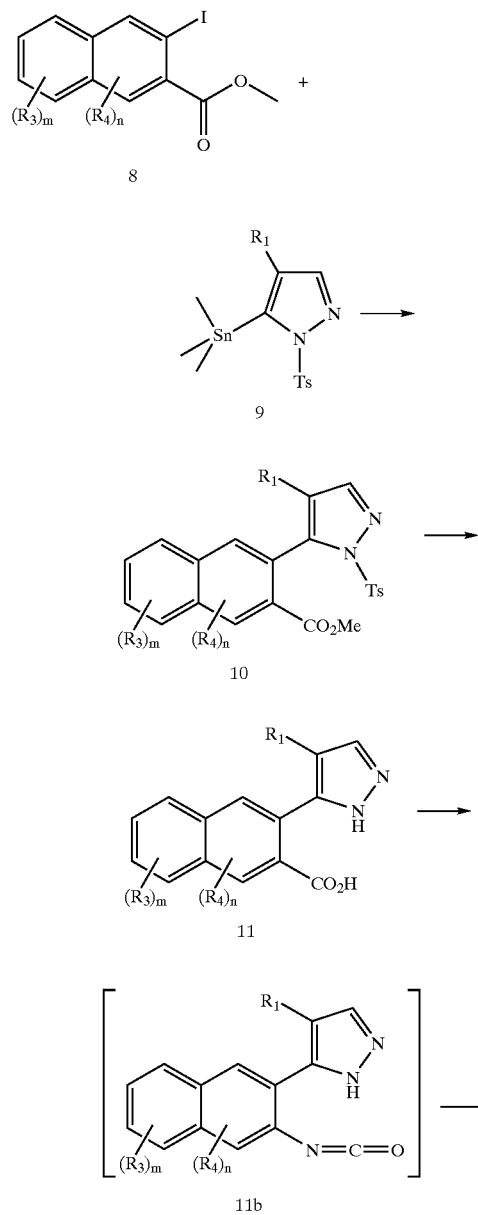

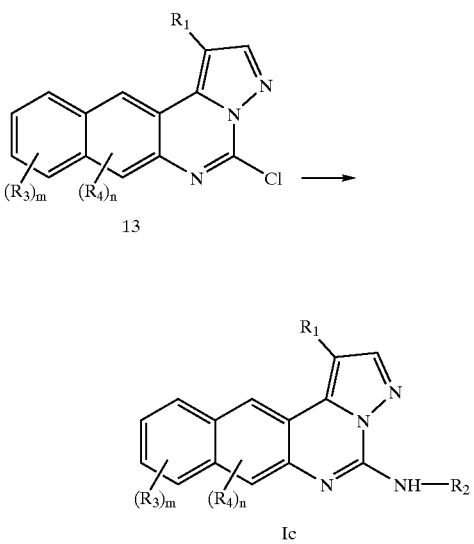

Benzo-pyrazolo-quinazolines of formula Ic (wherein $Y_2$ of formula I is N, X is $CHR_1$ and $R_1$ is as defined above) may be prepared as shown in Scheme III. Reagents 8c and 9c are condensed in the presence of catalyst in a Stille-type reaction to give coupled product 10, which is hydrolyzed to give compound 11. Treatment of 11 with, for example, diphenyl phosphoryl azide followed by heat, produces an intermediate isocyanate 11b, which will spontaneously cyclize under the reaction conditions to give compound 12. Treatment of 12 with a chlorinating agent gives chloro compound 19, which may be reacted with suitable primary amines ($R_2$—$NH_2$) to give compounds of formula Ic.

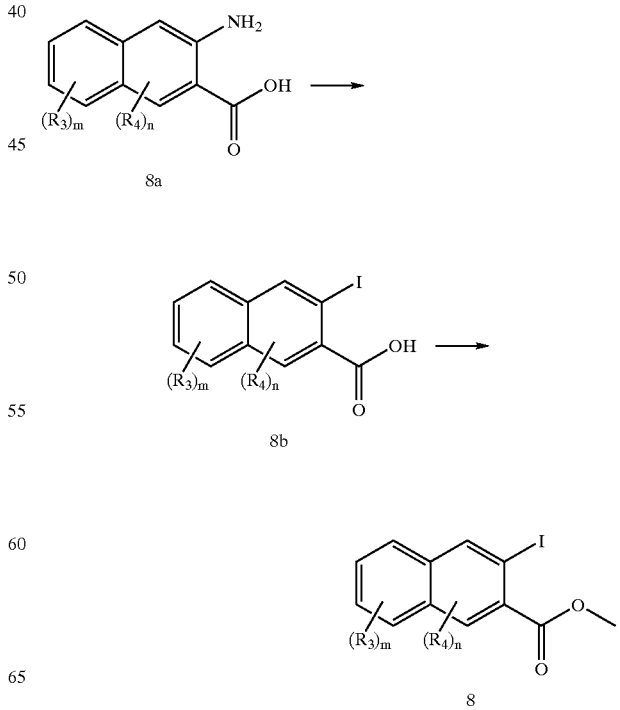

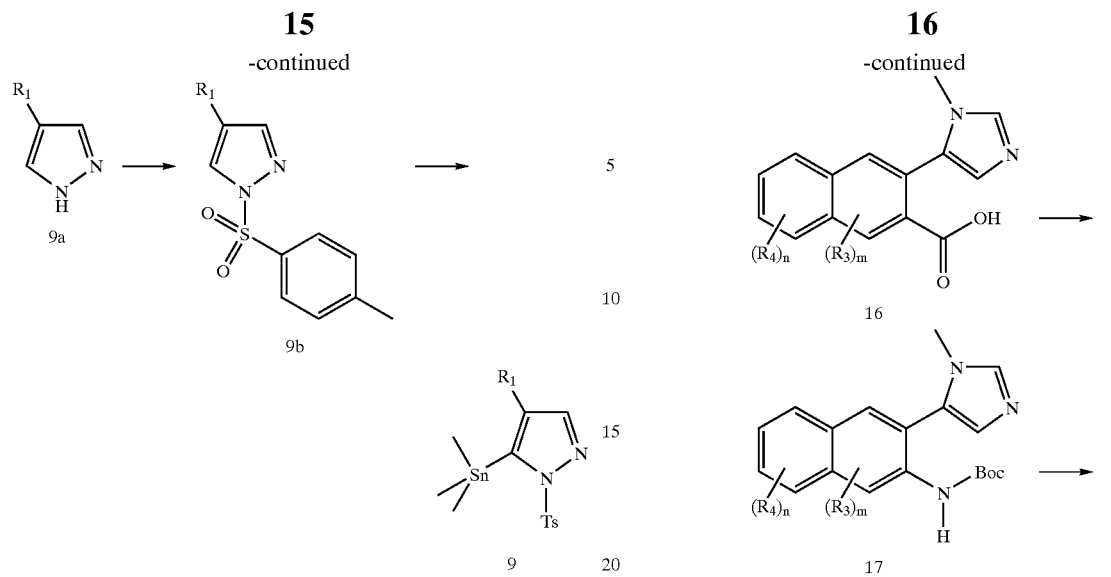

Reagents 8 and 9 for Scheme III above may be prepared as shown in Scheme IIIa. Substituted 3-amino-2-naphthoic acids 8a may be converted to substituted 3-iodo-2-naphthoic acids 8b by, for example, diazotization followed by treatment with an iodide salt. Esterification of compound 8b produces 3-iodo-2-napthoic acid esters 8. 4-Substituted pyrazoles 9a may be treated with a p-toluenesulfonating agent, such as p-toluenesulfonyl chloride, to give p-toluenesulfonamide 9b. Deprotonation of compound 9b with a strong base, such as t-butyl lithium, and treatment with a stannylating agent, such as trimethyl chloro stannane, gives reagent 9.

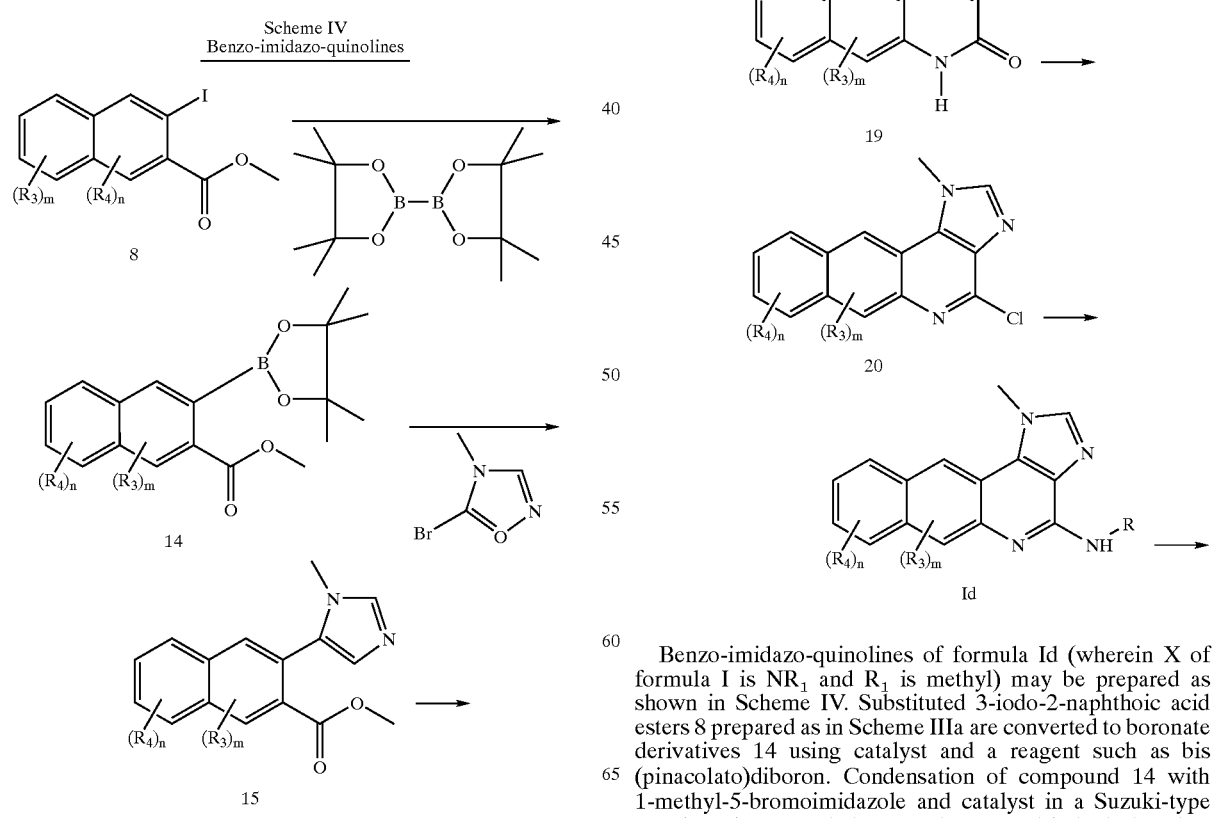

Benzo-imidazo-quinolines of formula Id (wherein X of formula I is $NR_1$ and $R_1$ is methyl) may be prepared as shown in Scheme IV. Substituted 3-iodo-2-naphthoic acid esters 8 prepared as in Scheme IIIa are converted to boronate derivatives 14 using catalyst and a reagent such as bis (pinacolato)diboron. Condensation of compound 14 with 1-methyl-5-bromoimidazole and catalyst in a Suzuki-type reaction gives coupled ester 15. Ester 15 is hydrolyzed to give acid 16, which is converted via treatment with diphenylphosphoryl azide (through an intermediate isocyanate—see 11b) and t-butanol into protected amine 17. Acid treatment converts 17 to free amine 18, which is heated in a high-boiling point inert solvent such as 1,2-dichlorobenzene with carbonyldiimidazole to give cyclized product 19. Treatment with a chlorinating agent converts compound 19 to the chloro derivative 20, which may be converted by treatment with suitable primary amines (R$_2$—NH$_2$) to give compounds of formula Id.

Scheme V
Benzo(g)thiozolao(4,5-c)quinolines

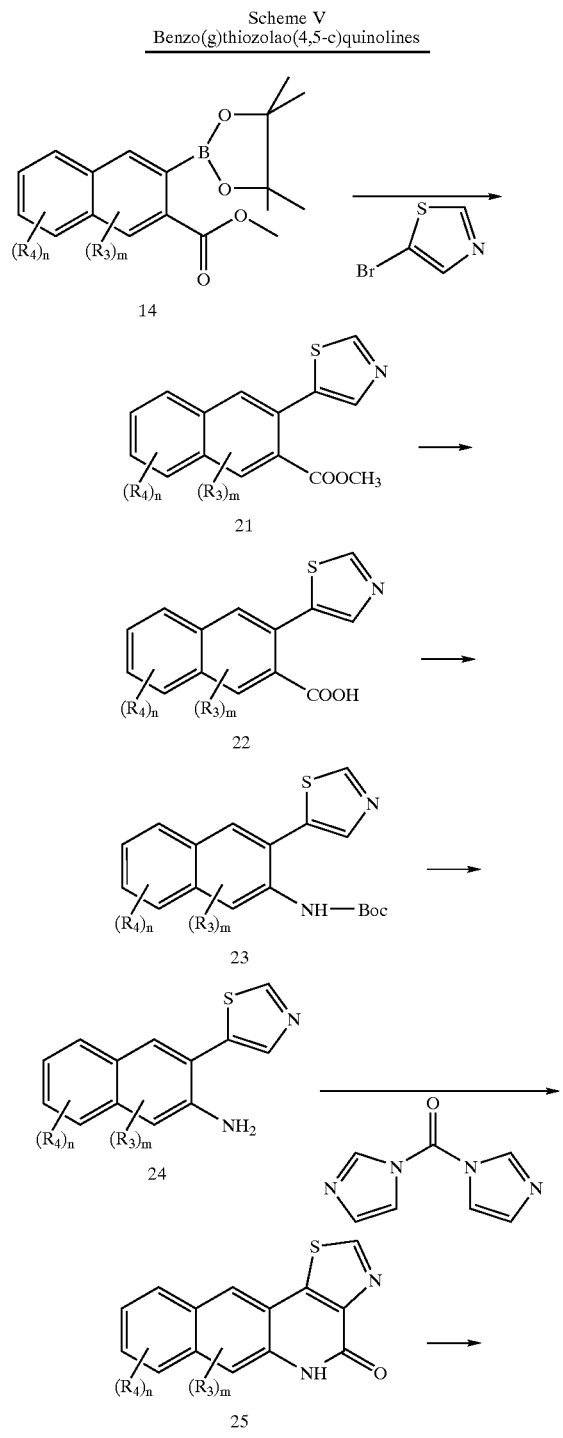

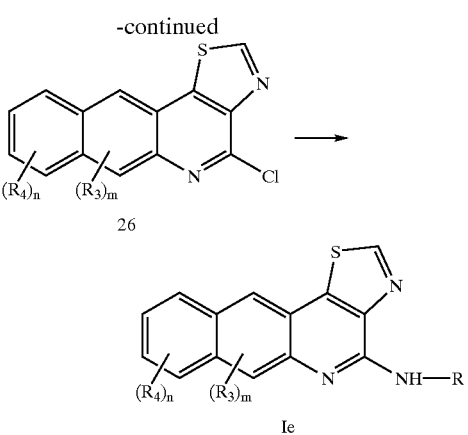

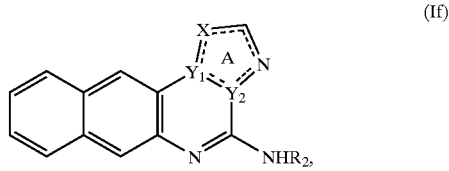

Benzo-thiazolo-quinolines may be prepared as shown above in Scheme V. Substituted 3-boronato-2-naphthoic acid ester 14 is condensed with 5-bromothiazole in a Suzuki-type reaction, catalyzed by a metal such as Pd, to give coupled product 21. The ester 21 is hydrolyzed under standard conditions to give acid 22, which is then converted via treatment with diphenylphosphoryl azide (through an intermediate isocyanate similar to 11b) and t-butanol into the protected amine 23. Acid treatment can convert compound 23 to the free amine 24, which is heated in a high-boiling inert solvent such as 1,2-dichlorobenzene with carbonyidiimidazole to give cyclized product 25. Compound 25 may be converted to the chloro derivative 26 by treatment with a chlorinating agent, and compound 26 is converted by treatment with suitable primary amines (R$_2$—NH$_2$) to give the compound of formula Ie.

Preferred Compounds

Preferred compounds of this invention are those having the formula (If):

(If)

and pharmaceutically-acceptable salts thereof, wherein
X is NR$_1$, CR$_1$, or S;
Y$_1$ and Y$_2$ are nitrogen or carbon, provided that
a) when X is CR$_1$, one of Y$_1$ and Y$_2$ is nitrogen, and b) when one of Y$_1$ and Y$_2$ is carbon, either the other of Y$_1$ and Y$_2$ is nitrogen or X is NR$_1$ or S, so that ring A defines a five-membered heteroaryl ring having two heteroatoms;
R$_1$ is hydrogen, halogen, lower alkyl, or substituted lower alkyl;
R$_2$ is alkyl or substituted alkyl.
More preferred are the compounds of formula (If), above, and/or pharmaceutically acceptable salts thereof, wherein
X is NR$_1$ or CR$_1$;
R$_1$ is hydrogen, halogen, lower alkyl, or trifluoromethyl;
R$_2$ is C$_{1-2}$ alkyl optionally substituted with OR$_9$ or NR$_{10}$R$_{11}$;
R$_9$ is hydrogen or lower alkyl; and $R_{10}$ and $R_{11}$ are (i) independently selected from hydrogen, $C_{1-2}$alkyl, $C_{1-2}$substituted alkyl, and —(C=O)$C_{1-2}$ alkyl, or alternatively (ii) together form a five to six membered heterocycle or heteroaryl.

Most preferred are the compounds of formula (If), above, and/or pharmaceutically acceptable salts thereof, wherein ring A is selected from:

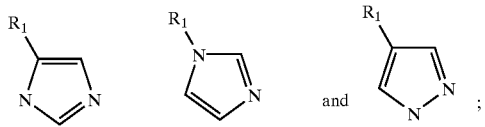

$R_1$ is hydrogen, halogen, ethyl, methyl, or trifluoromethyl; and $R_2$ is a $C_{1-2}$ alkyl optionally substituted with one of: OH, NH$_2$, NH($C_{1-2}$alkyl), N($C_{1-2}$alkyl)$_2$, NH($C_{1-2}$ substituted alkyl), N($C_{1-2}$substituted alkyl)$_2$, NH(C=O) $C_{1-2}$alkyl, and piperidinyl.

Advantageously, $R_1$ does not include hydroxy or an alkyl substituted with hydroxy.

Utility

The compounds and compositions of this invention are useful in treating conditions that are characterized by release of NF-κB and/or enhanced levels of TNF-α. The term "treating" or "treatment" denotes prevention, partial alleviation, or cure of the disease. Inhibition or suppression of NF-κB and/or TNF-α (may occur locally, for example, within certain tissues of the subject, or more extensively throughout the subject being treated for such a disease. Inhibition or suppression of NF-κB and/or TNF-α may occur by one or more mechanisms, e.g., by inhibiting or suppressing any step of the pathway(s) such as inhibition of IKK. The term "NF-κB-associated condition" refers to diseases that are characterized by release of NF-κB from the cytoplasm (e.g., upon phosphorylation of IKB). The term "TNF-α-associated condition" is a condition characterized by enhanced levels of TNF-α. In the instant specification, the term NF-κB-associated condition will include a TNF-α-associated condition but is not limited thereto as NF-κB is involved in the activity and upregulation of other pro-inflammatory proteins and genes. The term "inflammatory or immune diseases or disorders" is used herein to encompass both NF-κB-associated conditions and TNF-α-associated conditions, e.g., any condition, disease, or disorder that is associated with release of NF-κB and/or enhanced levels of TNF-α, including each of the conditions specifically referenced below.

The inventive compounds and compositions are useful for treating a variety of diseases including, but not limited to, treatment of transplant rejections (e.g., kidney, liver, heart, lung, pancreas, bone marrow, cornea, small bowel, skin allografts, skin homografts and heterografts, etc.); rheumatoid arthritis, psoriatic arthritis, multiple sclerosis, inflammatory bowel disease (such as Crohn's disease and ulcerative colitis); antiviral and autoimmune diseases including herpes simplex type 1 (HSV-1), herpes simplex type 2 (HSV-2), cytomegalovirus, Epstein-Barr, human immunodeficiency virus (HIV), Addison's disease (autoimmune disease of the adrenal glands), idiopathic adrenal insufficiency, and autoimmune polyglandular disease (also known as autoimmune polyglandular syndrome); Alzheimer's, Parkinson's, and Creutzfeldt-Jacob diseases; septic shock; hematopoiesis; inflammatory diseases such as osteoarthritis, acute pancreatitis, and chronic pancreatitis; inflammatory disorders of the central nervous system, including HIV encephalitis, cerebral malaria, and meningitis, atherosclerosis, and ataxia telangiectasis; respiratory allergies including asthma, hayfever, and allergic rhinitis; psoriasis, glomerulonephritis, serum sickness, lupus (systematic lupus erythematosis), urticaria, scleraclerma, contact dermatitis, dermatomyositis, alopecia, atopic eczemas, ichthyosis; and fungal infections such as mycosis fungoides. The inventive compounds are also effective in treating oncological diseases, in treating cancer and tumors, such as solid tumors, lymphomas and leukemia, and in particular, breast cancer, prostate cancer, and Hodgkin's lymphoma.

The present invention thus provides methods for treating such conditions, comprising administering to a subject in need thereof an effective amount of at least one compound of formula I or a salt thereof. Other therapeutic agents such as those described below may be employed in combination with the compounds of formula I. In the methods of the present invention, such other therapeutic agent(s) may be administered prior to, simultaneously with, or following the administration of the inventive compound.

The present invention also provides pharmaceutical compositions capable of treating conditions that are related to the activity of NF-κB, TNF-α, and/or enzymes modulating NF-κB and/or TNF-α levels such as IKK. The inventive compositions may contain other therapeutic agents and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment;

rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like, subject NF-κB and/or TNF-α associated conditions.

The inventive compounds and compositions may be employed alone or in combination with each other and/or other suitable therapeutic agents useful in treating NF-κB and TNF-α associated conditions. Exemplary of such other therapeutic agents include corticosteroids, rolipram, calphostin, CSAIDs, 4-substituted imidazo [1,2-A] quinoxalines as disclosed in U.S. Pat. No. 4,200,750 and Ceccarelli et al., supra; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof; and other cancer drugs and treatments, including radiation treatments and daunorubicin.

The above other therapeutic agents, when employed in combination with the compounds of the present invention, may be used, for example, in those amounts indicated in the Physicians' Desk Reference (PDR) or as otherwise determined by one of ordinary skill in the art.

Assays

TNFα Production

THP-1 (human monocytic cell line) obtained from ATCC was cultured in RPMI-1640 supplemented with 10% FBS, sodium pyruvate, HEPES, 2-mercaptoethanol, Penicillin/Streptomycin. To a 96-well plate containing THP-1 cells ($1.4 \times 10^6$/mL, $2.5 \times 10^5$ cells/well) in 180 $\mu$L RPMI-1640 was added 20 $\mu$L of the test compound in 10% DMSO. Typically, test compound concentrations of 0.1–100 $\mu$M were used in the assay. After one hour at 37° C., 20 $\mu$L of 1000 ng/mL lipopolysaccharide (LPS from Salmonella typhosa, Sigma) was added to each well. After an additional 6 hours at 37° C., the supernatants were collected following a 5 minute centrifugation of the plate to pellet the cells. The amount of TNFα in these supernatants was then measured using a TNFα-specific ELISA (Pharmingen). After subtracting out the amount of TNFα in a control that had not been treated with LPS, the percent inhibition was calculated versus a control that was treated with LPS but with no test compound added. $IC_{50}$ values were calculated from the percentage inhibition at various doses. Compounds of Examples 1–8 demonstrated $IC_{50}$ values of below 9 $\mu$M, with preferred and more preferred compounds having $IC_{50}$ values of below 2 $\mu$M and 1 $\mu$M, respectively.

TNFα-Stimulated Degradation of IκBα in THP-1 Cells

TNFα stimulation of monocytic THP-1 cells leads to the proteolytic degradation of IκBα. Both an IKK-dependent phosphorylation and ubiquitin ligase-dependent ubiquitination of IκBα are essential steps in the TNFα-stimulated pathway targeting IκBα for proteolytic degradation by the proteosome. THP-1 cells were suspended in RPMI-1640 supplemented with 10% fetal bovine serum, preincubated for 60 mins with test agent, then stimulated for 15 mins with TNFα (100 ng/mL, R&D Systems). Total cell lysates were fractionated by sodium dodecylsulfate-polyacrylamide electrophoresis followed by Western blot analysis. IκBα was detected using a polyclonal antibody from Santa Cruz (catalog #sc-4094) and ECL reagents (Amersham). Films were scanned using a Kodak ID Image Analysis system to quantitate the amount of IκBα. Compounds of formula (I) demonstrate up to 100% inhibition of the TNFα-induced degradation of IκBα in THP-1 cells at 10 $\mu$M.

LPS-Induced Serum TNFα in Mice

As a measure of activity against NF-κB-dependent TNFαproduction in vivo, test compounds were administered to BALB/c mice subsequently challenged with an intravenous dose of E. coli LPS (1 $\mu$g in 100 $\mu$L phosphate-buffered saline). 1 hour after LPS challenge, blood was collected from the mice and the levels of TNFα in the serum measured by EIA (R&D Systems). Inhibition was calculated from control animals which received LPS challenge with no test compound. Compounds of formula (I) demonstrated inhibition of the LPS-induced serum TNFα levels in vivo in the range of about 30 to 65% at 10 mg/kg, p.o; in the range of about 70 to 90% at 30 mg/kg p.o.; and in the range of above 90% at 100 mg/kg p.o.

Accordingly, compounds of formula (I) have been tested and shown activity as inhibitors of TNF-α and the NF-κB pathway.

The following Examples illustrate embodiments of the invention and are not intended to limit the scope of the claims. The reagents and starting materials of Preparations 1–19 are useful in synthesizing compounds of formula I, or salts thereof, such as illustrated in Schemes I-V. In the following Examples, anhydrous reactions were performed under an atmosphere of nitrogen or argon using either commercially available dry solvents or freshly distilled solvents. Melting points were determined in an open capillary tube with a Thomas-Hoover melting point apparatus. Column chromatography was performed using EM Science silica gel 60 (230–400 mesh) with the designated solvent system as eluant. Thin-layer chromatography was done on E. Merck silica gel 60 $F_{254}$ plates (0.5 mm). HPLC purity determinations were done using either an HP 1090 DR5 with a diode array detector and a Waters Nova-Pak C18 column (3.9×150 mm), or a Shimadzu LC-10AS with a SPD-10AV UV-Vis detector and one of the following columns: YMC Combiscreen ODS-A (4.6×50 mm); HP Zorbax SB-C18 (4.6×750 mm). Infrared spectra and $^1$HNMR spectra were recorded and chemical shifts are expressed in parts per million (ppm or δ) with the solvent in use as internal standard. Coupling constants are given in Hertz and multiplets are designated as follows; singlet (s), doublet (d), triplet (t), quartet (q), muliplet (m), and broad (br). Low resolution mass spectra were determined on a Finnigan Matt TSQ-7000 triple stage quadrapole spectrometer (positive/negative ESI) operated in the negative ion mode.

Preparation of Reagents and Starting Materials

Preparation 1

1,4-Dihydrobenzo[g]quinxalin-2,3-dione

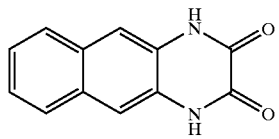

A mixture of 2,3-diaminonaphthalene (2.87 g, 18.14 mmol) and diethyl oxalate (30 mL, 223 mmol) was heated to reflux for 14 hours, cooled to RT and filtered. The residue was washed with EtOH and dried in vacuo to give the title compound as a brown solid (3.15 g, 82%); mp>350° C.; IR (KBr, cm$^{-1}$) 3045, 2942, 2869, 1716, 1642, 1406, 877; $^1$H NMR (DMSO) δ 12.11 (s, 2H), 7.84–7.81 (m, 2H), 7.54 (s, 2H) 7.39 (dd, J=6.3, 3.0, 2H); LC/MS 92.5% (220 nm), m/z (M+H$^+$) 213.

Preparation 2

2,3-Dichlorobenzo[g]quinoxaline

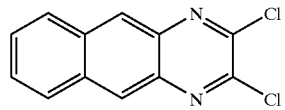

1 g (4.72 mmol) of 1,4-dihydrobenzo[g]quinoxalin-2,3-dione was stirred in 2 ml of phosphorus oxychloride for 5 hours at reflux. The mixture was concentrated by evaporation and dried under high vacuum. A sat'd K$_2$CO$_3$ solution was carefully added to the residue, and the solid was filtered off and washed with water to afford the title compound as a brown solid (1.00 g, 85%); mp 239–242° C.; IR (KBr, cm$^{-1}$) 1200, 1109, 998, 886, 748; $^1$H NMR (DMSO) δ 8.78 (s, 2H), 8.31–8.28 (m, 2H), 7.75–7.73 (m, 2H).

Preparation 3

2-Chloro-3-(propargylamino)benzo[g]quinoxaline

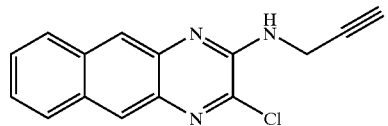

A mixture of 2,3-dichlorobenzo[g]quinoxaline (0.634 g, 2.55 mmol), propargylamine (0.21 ml, 3.05 mmol) and TEA (0.53 mL, 3.83 mmol) in 15 mL of dioxane was heated to reflux for 4.5 hours. After evaporating the resulting mixture under vacuum, the crude product was chromatographed (CH$_2$Cl$_2$) to afford the title compound as a yellow solid (0.496 g, 73%); mp 169–172° C.; IR (KBr, cm$^{-1}$) 3412, 3283, 3235, 1570, 1508, 1335; $^{-1}$H NMR (DMSO) δ 8.44 (s, 1H), 8.26 (s,1H), 8.16–8.06 (m, 3H), 7.58–7.54 (m, 1H), 7.51–7.48 (m, 1H), 4.28 (dd, J=6.1, 2.5, 2H), 3.12 (t, J=2.5, 1H); LC/MS 97.8% (220 nm), m/z (M+H$^+$) 268.

Preparation 4

4-Chloro-1-methylbenzo[g]imidazo[1,2-a]quinoxaline

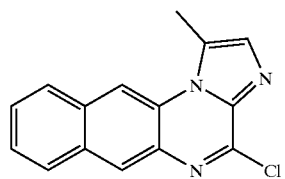

2-Chloro-3-(propargylamino)benzo[g]quinoxaline (0.420 g, 1.57 mmol) was treated with 4 mL of concentrated H$_2$SO$_4$ and the mixture was stirred at 80° C. for 1 hour, cooled to RT and poured into ice water. The mixture was cautiously neutralized with aqueous NaOH, and the resulting precipitate was filtered, washed with water, and dried in vacuo to give the title compound as a beige solid (0.124 g, 30%); mp 221–223° C.; IR (KBr, cm$^{-1}$) 1538, 1479, 1456, 1398, 1101, 919; $^1$H NMR (DMSO) δ 8.79 (s, 1H), 8.53 (s, 1H), 8.23 (d, J=8.1, 1H), 8.13 (d, J=8.5, 1H), 7.69–7.59 (m, 3H), 3.04 (s, 3H); LC/MS 100% (220 nm), m/z (M+H$^+$) 268.

Preparation 5

3-Iodo-2-napthoic acid

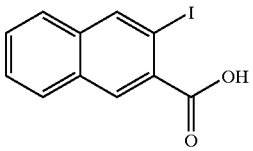

To a beaker of 3-amino-2-napthoic acid (6.01 g, 80% pure; 25.69 mmol), was added a solution of concentrated HCl (10.0 mL) and water (15.0 mL). After the resulting pink paste was stirred for 17 min, it was cooled to 0° C. and treated with a solution of water (10 mL) and NaNO₂ (2.54 g, 36.81 mmol) drop-wise (over 8 min). One minute later, the brown reaction mixture was treated with a cooled (0° C.) water (10.0 mL) solution of KI (10.0 g, 60.24 mmol) drop-wise (over 12 min). The cooling bath was removed, water (15 mL) was added, and the reaction mixture was stirred for 10 min at RT and heated at 95° C. for 65 min. It was then diluted with water (50 mL) and extracted with EtOAc (250 mL). The organic layer was washed with water (50 mL) and brine, dried (MgSO₄), filtered, and evaporated in vacuo. The resultant crude material was submitted to flash chromatography (sample was loaded as a silica gel mesh; EtOAc) to afford the title compound as an iodine colored fluffy solid weighing ~6.50 g. ¹H NMR (DMSO, δ=2.50): 13.36 (br s, 1H), 8.63 (s, 1H), 8.37 (s, 1H), 8.05 (d, J=7.9, 1H), 7.93 (d, J=8.0, 1H), 7.67–7.60 (m, 2H).

Preparation 6

Methyl 3-Iodo-2-napthoate

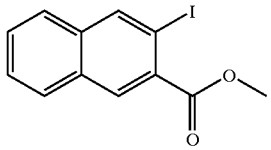

To 3-iodo-2-napthoic acid (Preparation 5) (6.50 g), were added MeOH (100 mL) and concentrated H₂SO₄ (2 mL), and the resultant heterogeneous mixture was refluxed for 13 hr. The reaction mixture was allowed to cool to RT, then neutralized with NaHCO₃ (6.0 g), and the volatile component was removed in vacuo. The residue was partitioned between water (50 mL) and EtOAc (300 mL). The organic layer was washed with Na₂S₂O₃ solution (4.2 g+50 mL of water) and brine, dried (MgSO₄), filtered and evaporated in vacuo. The resulting crude material was submitted to flash chromatography (sample was loaded as a silica gel mesh; 10% EtOAc/hexanes) to isolate the title compound as a light-yellow solid (5.50 g, 2 steps combined yield of 69%). ¹H NMR (DMSO, δ=2.50): 8.66 (s, 1H), 8.39 (s, 1H), 8.06 (d, J=8.0, 1H), 7.95 (d, J=8.0, 1H), 7.69–7.62 (m, 2H), 3.91 (s, 3H). (DCl) m/z (M+H)⁺=313.0. Anal. Calcd for C₁₂H₉IO₂: C, 46.18; H, 2.91. Found: C, 46.28; H, 2.85.

Preparation 7

4-Methyl-1-(4-toluenesulfonyl)pyrazole

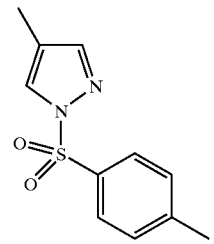

p-TsCl (9.81 g, 51.46 mmol) was added in batches over a few minutes to a CH₂Cl₂ (100 mL) solution of 4-methylpyrazole (4.00 g, 48.72 mmol) and pyridine (6.0 mL, 74.18 mmol). The reaction mixture was stirred for 95 min, then diluted with CH₂Cl₂ (250 mL) and washed with NaHCO₃ solution [a mixture of sat'd NaHCO₃ solution (20 mL) and H₂O (40 mL)], and water (60 mL). The organic layer was dried (MgSO₄), filtered and evaporated in vacuo. The resulting crude material was purified by flash chromatography (sample was loaded as a silica gel mesh; CH₂Cl₂) to afford the title compound as a white solid (10.88 g, 95%). ¹H NMR (CDCl₃, δ=7.26): 7.87 (d, J=8.4, 2H), 7.84 (s, 1H), 7.54 (s, 1H), 7.32 (d, J=8.40, 2H), 2.41 (s, 3H), 2.06 (s, 3H). (ESI) m/z (M+H)⁺=236.7. Anal. Calcd for C₁₁H₁₂N₂O₂S: C, 55.91; H, 5.12; N, 11.86. Found: C, 55.81; H, 4.94; N, 11.76.

Preparation 8

4-Methyl-1-(4-toluenesulfonyl)-5-trimethylstannylpyrazole

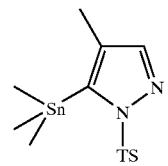

t-BuLi (1.7 M/pentane) was added over 10 min to a cooled (−78° C.) THF (60 mL) semi-suspension of 4-methyl-1-(4-tolunesulfonyl)pyrazole (Preparation 7) (6.01 g, 25.43 mmol). After the mixture was stirred for 10 min, it was treated drop-wise (over 20 min) with Me₃SnCl (28.0 mL of 1.0 M/THF, 28.0 mmol). The resulting mixture was stirred for 4.3 hr while the bath was allowed to thaw to −55° C., and then for 70 min. at RT. The reaction mixture was diluted with EtOAc (250 mL) and washed with water (50 mL) and brine, dried (MgSO₄), filtered, and evaporated in vacuo. The crude material was submitted to flash chromatography (sample was loaded as a silica gel mesh; 15–20% EtOAc/hexanes) to afford the title compound as a dense white solid (4.406 g, 43%). Non-consumed pyrazole of Preparation 7, above, was also retrieved (1.954 g, 33%). ¹H NMR of the title compound (DMSO, δ=2.50): 7.74 (s, 1H), 7.70 (d, J=8.3, 2H), 7.45 (d, J=8.3, 2H), 2.38 (s, 3H), 2.08 (s, 3H; satellite peaks due to Sn—H with J=4.5), 0.45 (s, 9H; satellite peaks due to Sn—H with J=59.8 and 57.3). (ESI) m/z (M+H)⁺=400.9.

Preparation 9

Methyl 3-(4-methyl-1-(4-toluenesulfonyl)pyrazol-5-yl)-2-naphthoate

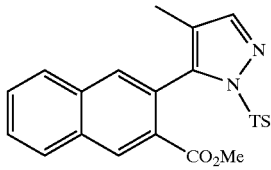

DMF (26.0 mL) was added into a mixture of methyl-3-iodo-2-napthoate (Preparation 6) (2.017 g, 6.463 mmol), 4-methyl-1-(4-tolunesulfonyl)-5-trimethylstannylpyrazole (Preparation 8) (2.895 g, 7.254 mmol), $Pd_2dba_3$ (236 mg, 0.258 mmol), $Ph_3As$ (317.2 mg, 1.036 mmol), and CuI (130.7 mg, 0.686 mmol). After nitrogen was bubbled through the heterogeneous mixture for a few minutes, it was stirred at RT for 7 min and at 90° C. for 12 hr. The volatile component was removed in vacuo, and the resultant viscous residue was submitted to flash chromatography (sample was loaded as a silica gel mesh; 0-10% $EtOAc/CH_2Cl_2$) to afford the titled compound as a yellow solid (1.485 g, 55%). $^1$H NMR (DMSO, δ=2.50): 8.73 (s, 1H), 8.23 (d, J=7.7, 1H), 8.05 (d, J=7.7, 1H), 7.83 (s, 1H), 7.81 (s, 1H), 7.77–7.71 (m, 2H), 7.50 (d, J=8.2, 2H), 738 (d, J=8.2, 2H), 3.66 (s, 3H), 2.38 (s, 3H), 1.77 (s, 3H). (ESI) m/z (M+H)$^+$=421.0.

Preparation 10

3-(4-Methylpyrazol-5-yl)-2-naphthoic acid

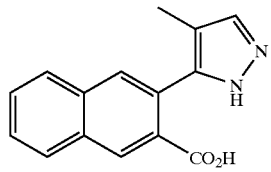

THF (12.0 mL), MeOH (8.0 mL) and NaOH solution (7.5 mL of 1.0 N/$H_2O$) were added to methyl-3-(4-methyl-1-(4-tolunesulfonyl)pyrazol-5-yl)-2-napthoate (Preparation 9) (1.240 g, 2.949 mmol), and the reaction mixture was heated at 80° C. for 4.2 hr. It was then diluted with water (20 mL), acidified to pH~4.5 with 1N HCl, and extracted with EtOAc (75 ml, 2×). The combined organic layer was washed with brine, dried ($MgSO_4$), filtered, and evaporated in vacuo The resulting crude material was submitted to flash chromatography (sample was loaded as a silica gel mesh; 10% MeOH/$CH_2Cl_2$) to isolate the title compound as faint-yellow solid (300 mg, 40%). $^1$H NMR (DMSO, δ=2.50; one tautomer was observed): 12.70 (br s, 2H), 8.37 (s, 1H), 8.08 (d, J=7.9, 1H), 8.01 (d, J=8.0, 1H), 7.93 (s, 1H), 7.65–7.58 (m, 2H), 7.47 (s, 1H), 2.01 (s, 3H). (ESI) m/z (M+H)$^+$=252.99.

Preparation 11

1-Methylbenzo(g)pyrazolo(1,5-c)quinazolin-5-one

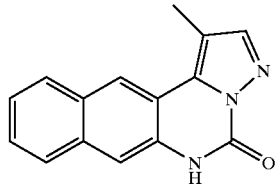

$Et_3N$ (300 μL, 2.152 mmol) and $(PhO)_2PON_3$ (440 μL, 2.064 mmol) were added to a $C_6H_6$ (10.0 mL) suspension of 3-(4-methylpyrazol-5-yl)-2-naphthoic acid (Preparation 10) (257 mg, 1.019 mmol), and the mixture was heated at 50° C. for 2 hr. The volatile component was removed in vacuo, and the resulting yellow solid was dissolved in o-dichlorobenzene (8.0 mL) and heated at 150° C. for 4 hr. During the latter heating, there was a gradual evolution of gas accompanied by the formation of a suspension. The reaction mixture was allowed to cool to RT, and the precipitate was filtered and washed with copious ether to afford the title compound as a fluffy light-yellow solid (170.8 mg, 67%). $^1$H NMR (DMSO, δ=2.50): 11.86 (s, 1H), 8.57 (s, 1H), 8.13 (d, J=8.2, 1H), 7.99 (s, 1H), 7.92 (d, J=8.3, 1H), 7.22 (s, 1H), 7.56 (app t, J=7.21, 1H), 7.49 (app t, J=7.48, 1H), 2.60 (s, 3H). (ESI) m/z (M+H)$^+$=250.00.

Preparation 12

1-Methyl-5-chlorobenzo(g)pyrazolo(1,5-c)quinazoline

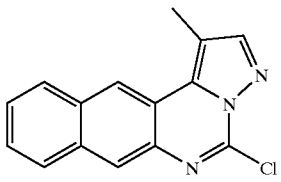

$PhNEt_2$ (1.50 mL) and $POCl_3$ (15.0 mL) were added to 1-methylbenzo(g)pyrazolo(1,5-c)quinazolin-5-one (Preparation 11) (184.7 mg, 0.741 mmol), and the resulting heterogeneous mixture was heated at reflux for 46 hr. During heating, the suspension (the starting material) gradually started to dissolve. The dark-green reaction mixture was filtered to remove non-consumed starting material (16.2 mg, 8.8%), and the filtrate was exposed to high vacuum to remove most of the $POCl_3$. The residue was partitioned between water (30 mL) and EtOAc (70 mL). The organic layer was washed with brine, dried ($MgSO_4$), filtered, and evaporated in vacuo. The crude material was submitted to flash chromatography (sample was loaded as a silica gel mesh; 20% EtOAc/hexanes) to afford the title chloride as an off-white solid (153 mg, 77%). $^1$H NMR (DMSO, δ=2.50): 8.80 (s, 1H), 8.46 (s, 1H), 8.29–8.27 (m, 1H), 8.19 (s, 1H), 8.17–8.15 (m, 1H), 7.70–7.65 (m, 2H), 2.70 (s, 3H). (ESI) m/z (M+H)$^+$=267.98.

Preparation 13

Methyl-3-(4,4,5,5-tetramethyl-1,3,2-dioxaborolan-2-yl)-2-naphthoate

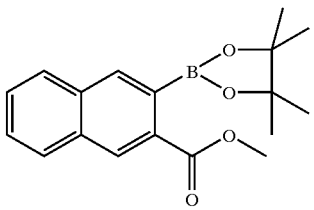

To a solution of 4,4,4',4',5,5,5',5'-octamethyl-2,2'-bi-1,3,2-dioxaborolane (30.0 g, 0.118 mol) and methyl 3-iodo-2-naphthoate (Preparation 6) (33.5 g, 0.107 mol) in DMSO (600 mL) were added PdCl$_2$ (dppf) (2.62 g, 0.21 mmol) and KOAc (31.51 g, 0.321 mol). The mixture was degassed and purged with N$_2$, and then heated at 85° C. for 18 hours. The brown reaction mixture was cooled to RT, diluted with water (1.5 L), and extracted with EtOAc (2.5 L, then 2×500 mL). The combined organic layer was washed with brine (9×500 mL), dried over MgSO$_4$, filtered and evaporated in vacuo. The resulting crude material was submitted to flash chromatography (2.0% MeOH/CHCl$_3$), affording the title compound as a yellow solid (19.5 g, 58%). $^1$H NMR (CDCl$_3$): 8.50(s, 1H), 7.99(s, 1H), 7.90(d, J=8.1, 1H), 7.86(d, J=8.1, 1H), 7.57(m, 1H), 7.54(m, 1H), 3.98(s, 3H), 1.47(s, 12H). (ESI) m/z (M+H)$^+$=313.16

Preparation 14

Methyl-3-(1-methyl-imidazol-5-yl)-2-naphthoate

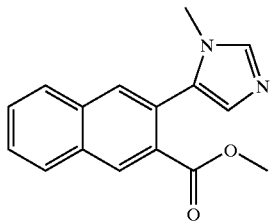

To a mixture of methyl-3-(4,4,5,5,-tetramethyl-1,3,2-dioxaborolan-2-yl)-2-naphthoate (Preparation 13) (15.37 g, 49.3 mmol) and 5-bromo-1-methyl-1H-imidazole (9.06 g, 49.3 mmol) in toluene/EtOH (350 mL/36 mL) were added Pd(PPh$_3$)$_4$ (11.37 g, 9.84 mmol), Na$_2$CO$_3$ (20.9 g, 197.2 mmol) and water (106 mL). The mixture was degassed, purged with N$_2$, and heated to reflux for 20 hours. It was then cooled to RT, neutralized with HCl (1.0 N, 100 mL), and concentrated in vacuo. The residue was partitioned between water (300 mL) and EtOAc (1 L). The organic layer was washed with water (2 L) and brine, dried over MgSO$_4$, filtered and evaporated in vacuo. The resulting crude material was submitted to flash chromatography (1.5% MeOH/CHCl$_3$), furnishing the title compound as a light-yellow solid (9.5 g, 72%). $^1$H NMR(CDCl$_3$): 8.53(s, 1H), 7.99(d, J=8.1, 1H), 7.80(d, J=8.1, 1H), 7.77(s, 1H), 7.56(m, 1H), 7.54(m, 1H), 7.54(s, 1H), 6.94(s, 1H), 3.73(s, 3H), 3.29(s, 3H). (ESI) m/z (M+H)$^+$=267.11.

Preparation 15

3-(1-Methyl-imidazol-5-yl)-2-naphthoic acid

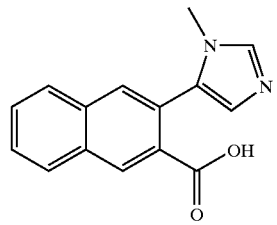

A solution of methyl-3-(1-methyl-imidazol-5-yl)-2-naphthoate (Preparation 14) (8.5 g, 32 mmol) in THF/MeOH (3/2, 120 mL) was treated with aqueous NaOH (1.0 N, 48 mL). After 20 hours at RT, it was neutralized with aqueous HCl (1.0 N, 20 mL). The solvent was evaporated in vacuo. The solid residue was treated with MeOH (5 mL), then evaporated again. The resulting crude material was purified by flash chromatography (5% MeOH/EtOAc) affording the title compound as a pale-yellow solid (6.0 g, 74%). $^1$H NMR(CDCl$_3$): 8.34 (s, 1H), 7.95 (d, J=8.1, 1H), 7.90 (d, J=8.1, 1H), 7.72 (s, 1H), 7.53 (s, 1H), 7.52 (m, 1H), 7.50 (m, 1H), 6.83 (s, 1H), 3.16 (s, 3H). (ESI) m/z (M+H)$^+$=253.10.

Preparation 16

1,1-Dimethylethyl-3-((1-methylimidazol-5-yl)-2-naphthyl)carbamate

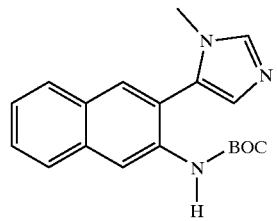

To a mixture of 3-(1-methyl-imidazol-5-yl)-2-naphthoic acid (Preparation 15) (1.0 g, 3.95 mmol) and Et$_3$N (1.1 mL, 7.91 mmol) in 20 ml t-BuOH was added diphenylphosphorylazide (1.63 g, 5.93 mmol). After 40 minutes at 80° C., the mixture was cooled to RT. The slurry was diluted with EtOAc (300 mL), and washed once with water (50 mL) and three times with brine. The organic layer was dried over MgSO$_4$, filtered, and evaporated in vacuo. The crude material was submitted to flash chromatography (0.5% MeOH/EtOAc) affording the title compound as a pale-yellow solid (0.67 g, 51%). $^1$H NMR(CDCl$_3$): 8.34(s, 1H), 7.95(d, J=8.1, 1H), 7.90(d, J=8.1, 1H), 7.72(s, 1H), 7.53(s, 1H), 7.52(m, 1H), 7.50(m, 1H), 6.83(s, 1H), 3.16(s, 3H), 1.43(s, 9H). (ESI) m/z (M+H)$^+$=324.15.

Preparation 17

5-(3-Amino-2-naphthyl)-1-methylimidazole

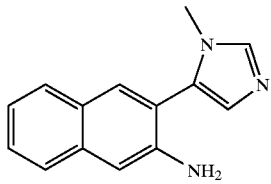

A solution of 1,1-dimethylethyl-3-((1-methylimidazol-5-yl)-2-naphthyl)carbamate (Preparation 16) (1.0 g, 2.98 mmol) in TFA/CH$_2$Cl$_2$ (1:10, 50 mL) was stirred at RT for 18 hours. After concentration, the residue was diluted with EtOAc (200 mL), washed with aqueous NaHCO$_3$ (100 mL) and brine. The organic layer was then dried over MgSO$_4$, filtered and evaporated in vacuo. The crude material was submitted to flash chromatography (5% MeOH/EtOAc) affording the title compound as a light yellow solid (0.49 g, 70%). $^1$H NMR(CDCl$_3$): 7.65(d, J=8.1, 1H), 7.59(d, J=8.1, 1H), 7.57(s, 1H), 56(s, 1H), 7.36(m, 1H), 7.22(m, 1H), 7.13(s, 1H), 7.03(s, 1H), 3.96(b, 2H), 3.46(s, 3H). (ESI) m/z (M+H)$^+$=224.08.

Preparation 18

1-Methyl-4,5-dihydrobenzo(g)imidazo(4,5-c)quinolin-4-one

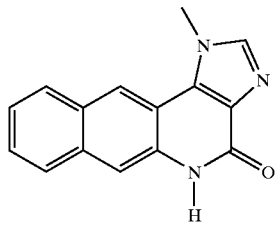

A mixture of 5-(3-amino-2-naphthyl)-1-methylimidazole (Preparation 17) (0.48 g, 2.14 mmol) and 1,1'-carbonyldiimidazole (0.42 g, 2.57 mmol) in o-dichlorobenzene (22 mL) was heated at 180° C. for 5 hours. The suspension was cooled to RT, filtered, and dried under vacuum, affording the title compound as a light yellow solid (0.22 g, 42%). $^1$H NMR(DMSO): 11.57(s, 1H), 8.71(s, 1H), 8.15(s, 1H), 8.10(d, J=8.4, 1H), 7.89(d, J=8.4, 1H), 7.84(s, 1H), 7.53(m, 1H), 7.46(m, 1H), 4.30(s, 3H). (ESI) m/z (M+H)$^+$=250.08.

Preparation 19

1-Methyl-4-chlorobenzo(g)imidazo(4,5-c)quiloline

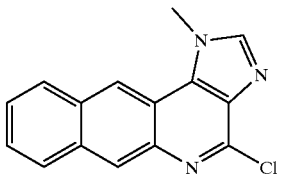

To a mixture of 1-methyl-4,5-dihydrobenzo(g)imidazo(4,5-c)quinolin-4-one (Preparation 18) (200 mg, 0.80 mmol) and PhNEt$_2$ (2.5 mL, 1.6 mmol) was added POCl$_3$ (8 mL). The mixture was then heated to reflux for 4 hours. After cooling, excess POCl$_3$ was removed under vacuum. The residue was diluted with EtOAc (150 mL), and treated with NaHCO$_3$ (1 g) to neutralize the acid. The organic layer was washed with brine, dried over MgSO$_4$, filtered and evaporated in vacuo. The crude material was submitted to flash chromatography (EtOAc) affording the title compound as a light yellow solid (0.18 g, 90%). $^1$H NMR(CDCl$_3$): 8.61(s, 1H), 8.57(s, 1H), 8.01(d, J=8.8, 1H), 7.98(d, J=8.8, 1H), 7.89(s, 1H), 7.57(m, 1H), 7.54(m, 1H), 4.35(s, 3H). (ESI) m/z (M+H)$^+$=268.08.

EXAMPLE 1

1-Methyl-4-methylaminobenzo[g]imidazo[1,2-a]quinoxaline

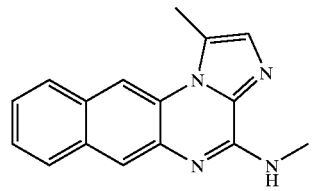

To a solution of 4-chloro-1-methylbenzo[g]imidazo[1,2-a]quinoxaline (0.063 g, 0.236 mmol) (Preparation 4) in 4 mL of THF was added MeNH$_2$ (40% in H$_2$O, 0.16 mL, 1.88 mmol). The reaction tube was sealed and the mixture stirred at 80° C. for 18 hours. The cooled mixture was then taken up in EtOAc, washed with water and brine, dried (Na$_2$SO$_4$) and evaporated. The resulting residue was recrystallized using i-PrOH to give Example 1 as beige needles (0.043 g, 69%); mp 201–202° C., IR (KBr, cm$^{-1}$) 3324, 1575, 1557, 1411, 1121; $^1$H NMR (DMSO) δ 8.62 (s, 1H), 8.10 (s, 1H), 8.08 (d, J=8.1, 1H), 7.94 (d, J=8.1, 1H), 7.77 (br d, J=4.5, 1H), 7.49–7.45 (m, 2H), 7.35 (s, 1H), 3.06 (d, J=4.6, 3H), 2.98 (s, 3H); MS ($^+$ESI, M+H$^+$) m/z 263; HPLC: 99.5% (230 nm); HRMS calcd for C$_{16}$H$_{14}$N$_4$: 262.1219; found 262.1226.

EXAMPLE 2

1-Methyl-4-(2-N-methylaminoethylamino)benzo[g]imidazo[1,2-a]quinoxaline hydrochloride

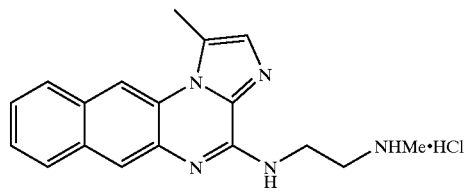

To a solution of 4-chloro-1-methylbenzo[g]imidazo[1,2-a]quinoxaline (0.075 g, 0.281 mmol) (Preparation 4) in 4 mL of THF was added N-methylethylene diamine (0.20 mL, 2.25 mmol). The reaction tube was sealed and the mixture stirred at 80° C. for 18 hours. The resulting cooled mixture was then taken up in EtOAc, washed with water and brine, dried (Na$_2$SO$_4$) and evaporated. Purifying the residue by preparative TLC (CH$_2$Cl$_2$:MeOH, 8:2) yielded 1-methyl-4-(2-N-methylaminoethylamino)benzo[g]imidazo[1,2-a]quinoxaline. This solid was dissolved in CH$_2$Cl$_2$/EtOH and a solution of 1N HCl in EtOH was added to form the hydrochloride salt, which was filtered, washed with EtOH and dried in vacuo to afford the above titled salt as an off-white solid (0.025 g, 26%); mp 265–275° C. dec; IR (KBr, cm$^{-1}$) 3448, 2958, 2780, 1656, 1532, 1420; $^1$H NMR (CD$_3$OD) 8.72 (s, 1H), 8.42 (s, 1H), 8.13–8.11 (m, 1H), 8.01–7.98 (m, 1H), 7.63–7.57 (m, 3H), 4.23–4.20 (m, 2H), 3.54–3.51 (m, 2H), 3.07 (s, 3), 286 (s, 3H); MS ($^+$ESI, M+H$^+$) m/z 306; HPLC: 98.3% (230 nm); HRMS calcd for C$_{18}$H$_{19}$N$_5$: 306.1719; found 306.1708.

EXAMPLE 3

1-Methyl-4-methylaminobenzo[g]pyrazolo[1,5-c]quinazoline

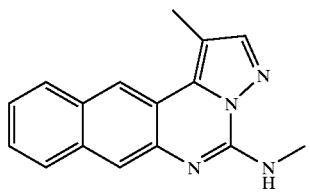

A mixture of 4-methyl-1-(4-toluenesulfonyl)-5-trimethylstannylpyrazole (Preparation 8) (24.0 mg, 0.0896 mmol) and MeNH$_2$ (3.0 mL of 2.0 M/THF, 6.0 mmol) in a pressure tube was heated at 60° C. for 5 hr. After the reaction mixture was cooled to RT, it was treated with NaHCO$_3$ (57 mg) and water (2 pipet-drops) and stirred for 5 min. Silica gel was added and the volatile component was removed in vacuo. The resulting silica gel mesh was submitted to flash chromatography (20% EtOAc/hexanes) to afford the title compound as a light yellow solid (23.0 mg, 98%). $^1$H NMR (DMSO, δ=2.50): 8.60 (s, 1H), 8.10 (s, d, J=8.3, 1H), 8.03 (s, 1H), 8.01 (s, 1H), 7.95 (d, J=8.01, 1H), 7.92 (q, J=4.7, 1H), 7.50 (t, J=7.5, 1H), 7.44 (t, J=7.4, 1H), 3.09 (d, J=4.7, 3H), 2.66 (s, 3H). (ESI) m/z (M+H)$^+$=263.02.

EXAMPLE 4

1-Methyl-4-(2-N-methylaminoethylamino)benzo[g]pyrazolo[1,5-c]quinazoline

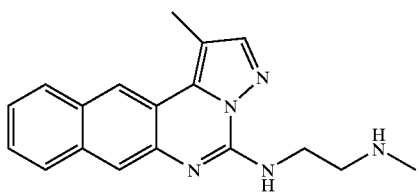

N-methyl-ethylenediamine (250 μL, 2.836 mmol) was added rapidly to a THF (2.0 mL) semi-suspension of 4-methyl-1-(4-toluenesulfonyl)-5-trimethylstannylpyrazole (Preparation 8) (30.5 mg, 0.114 mmol). The reaction mixture was stirred at RT for 1 hr and at 75° C. for 2.3 hr. After the reaction mixture was cooled to RT, it was treated with NaHCO$_3$ (57 mg) and water (2 pipet-drops) and stirred for a few minutes. The volatile components, including the excess diamine, were removed in vacuo. The crude material was submitted to flash chromatography (sample was loaded as a silica gel mesh; 0–100% MeOH/EtOAc) to afford the title compound as a yellow waxy-solid (43.4 mg; the weight is 8.6 mg more than the theoretical yield). $^1$H NMR (DMSO, δ=2.50): 8.60 (s, 1H), 8.10 (d, J=8.1, 1H), 8.02 (s, 2H, signal overlap), 7.95 (d, J=8.1, 1H), 7.73 (t, J=5.5, 1H), 7.51 (ddd, J=8.2, 6.8, 1.1, 1H), 7.45 (ddd, J=8.0, 6.9, 1.0, 1H), 3.66 (apt q, J=6.1, 2H), 2.82 (t, J 6.3, 2H), 2.66 (s, 3H), 2.35 (s, 3H), 1.81 (s, 1H). (ESI) m/z (M+H)$^+$=306.05.

EXAMPLE 5

1-Methyl-4-methylaminobenzo(g)imidazo(4,5-c)quinoline

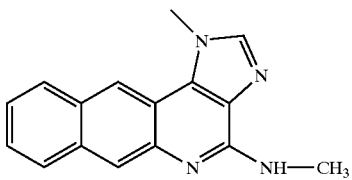

A mixture of 1-methyl-4-chlorobenzo(g)imidazo(4,5-c)quinoline (Preparation 19) (130 mg, 0.49 mmol) and MeNH$_2$ (2.0M/THF, 1.5 mL, 2.92 mmol) was heated in a pressure tube at 80° C. for 18 hours. After the reaction mixture was cooled to RT, it was diluted with EtOAc (100 mL), washed with sat'd NaCO$_3$ (50 mL), and brine. The organic layer was dried over MgSO$_4$, filtered and evaporated in vacuo. The crude material was submitted to flash chromatography (5% MeOH/EtOAc) affording the title compound as a pale white solid (5.2 mg, 4%). $^1$H NMR(CDCl$_3$): 8.44(s, 1H), 8.35(s, 1H), 7.94(d, J=8.3, 1H), 7.90(d, J=8.3, 1H), 7.72(s, 1H), 7.46(m, 1H), 7.40(m, 1H), 5.95(b, 1H), 4.28(s, 3H), 3.31(s, 3H). (ESI) m/z (M+H)$^+$=263.14.

EXAMPLE 6

1-Methyl-4-(2-N-methylaminoethylamino)benzo(g)imidazo(4,5-c)quinoline

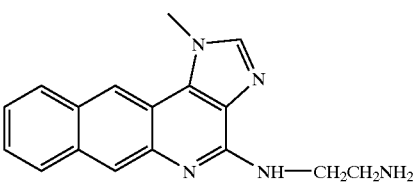

A solution of 1-methyl-4-chlorobenzo(g)imidazo(4,5-c)quinoline (Preparation 19) (130 mg, 0.49 mmol) in NH$_2$CH$_2$CH$_2$NH$_2$ (3.2 mL, 49 mmol), was heated at 60° C. for 18 hours. The solvent was evaporated in vacuo. The residue was diluted with EtOAc (50 mL) and washed with brine (20 mL). The organic layer was dried over MgSO$_4$, filtered, and concentrated. The crude material was submitted to flash chromatography (MeOH) affording the title compound as a pale white solid (6.9 mg, 5%). $^1$H NMR(CDCl$_3$): 8.52(s, 1H), 8.33(s, 1H), 7.96(d, J=8.3, 1H), 7.94(d, J=8.3, 1H), 7.77(s, 1H), 7.46(m, 1H), 7.42(m, 1H), 6.22(b, 1H), 4.36(s, 3H), 3.85(m, 2H), 3.10(m, 2H), 1.60(b, 1H). (ESI) m/z (M+H)$^+$=292.18.

EXAMPLE 7

1-Methyl-4-(2-hydroxyethylamino)benzo[g]imidazo[1,2-a]quinoxaline

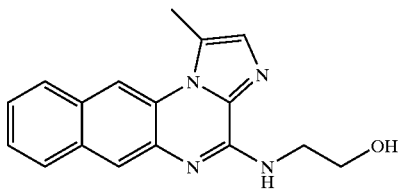

To a solution of 4-chloro-1-methylbenzo[g]imidazo[1,2-a]quinoxaline (0.060 g, 0.225 mmol) (Preparation 4) in 2 mL of THF was added 2-aminoethanol (0.11 mL, 1.80 mmol). The reaction tube was sealed and the mixture stirred at 80° C. for 16 hours. The resulting cooled mixture was then taken up in EtOAc, washed with water and brine, dried ($Na_2SO_4$) and evaporated. The resulting residue was recrystallized using i-PrOH to give Example 7 (0.062 g, 94%); mp 186–188° C.; IR (KBr, $cm^{-1}$) 3370, 3147, 1549, 1485, 1414; $^1$H NMR (DMSO-d6) 8.64 (s, 1H), 8.10–8.09 (m, 2H), 7.96 (d, J=7.5, 1H), 7.51–7.46 (m, 3H), 7.37 (s, 1H), 4.91 (t, J=5.2, 1H), 3.70–3.66 (m, 4H), 3.00 (s, 3H); MS ($^+$ESI, M+H$^+$) m/z 293; HPLC: 98.8% (230 nm).

EXAMPLE 8

1-Methyl-4-(2-piperidin-1-yl-ethylamino)benzo[g]imidazo[1,2-a]quinoxaline

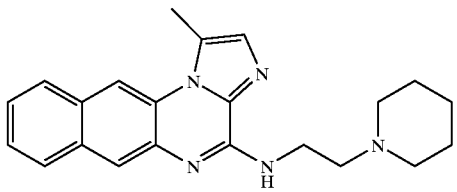

To a solution of 4-chloro-1-methylbenzo[g]imidazo[1,2-a]quinoxaline (0.055 g, 0.206 mmol) (Preparation 4) in 5 mL of THF was added 1-(2-aminoethyl)piperidine (0.24 mL, 1.65 mmol). The reaction tube was sealed and the mixture stirred at 80° C. for 17 hours. The resulting cooled mixture was then taken up in EtOAc, washed with water and brine, dried ($Na_2SO_4$) and evaporated. The resulting residue was recrystallized using i-PrOH to give Example 8 (0.063 g, 84%); mp 170–172° C.; IR (KBr, $cm^{-1}$) 3300, 2932, 1557, 1483, 1408; $^1$H NMR (DMSO-d6) 8.61 (s, 1H), 8.07–8.06 (m, 2H), 7.94 (d, J=7.6, 1H), 7.49–7.34 (m, 4H), 3.66 (br q, J=6.5, 2H), 2.97 (s, 3H), 2.59 (br t, J=6.5, 2H), 2.44 (br s, 4H), 1.54–1.39 (m, 6H); MS ($^+$ESI, M+H$^+$) m/z 360; HPLC: 97.6% (230 nm).

It should be understood that one skilled in the field may make various modifications to the compounds, compositions and schemes described above, applying the ordinary level of skill in the field, without departing from the spirit or scope of the invention. All such modifications are intended to be included within the invention as defined in the appended claims.

We claim:

1. A compound of the formula:

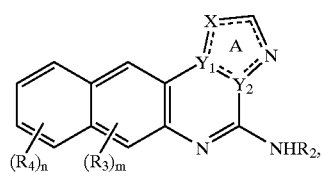

(I)

or a pharmaceutically-acceptable salt thereof, wherein

X is $NR_1$, $CR_1$, or S;

$Y_1$ and $Y_2$ are nitrogen or carbon, provided that
a) when X is $CR_1$, at least one of $Y_1$ and $Y_2$ is nitrogen, and b) when one of $Y_1$ and $Y_2$ is carbon, the other of $Y_1$ and $Y_2$ is nitrogen and/or X is $NR_1$ or S, so that ring A defines a five-membered heteroaryl ring having at least two heteroatoms;

$R_1$ is hydrogen, halogen, alkyl, substituted alkyl, cyano, $OR_5$, $NR_5R_6$, C(=O)$R_5$, $CO_2R_5$, or aryl;

$R_2$ is alkyl, substituted alkyl, alkenyl, alkynyl, alkoxy, alkylthio, aryl, heteroaryl, heterocyclo, cycloalkyl, or substituted cycloalkyl;

$R_3$ and $R_4$ are independently selected from halogen, alkyl, substituted alkyl, nitro, cyano, $OR_7$, $NR_7R_8$, C(=O)$R_7$, $CO_2R_7$, $SR_7$, C(=O)$NR_7R_8$, $NR_7C(=O)_8$, $NR_7C(=O)OR_8$, $S(O)_qR_7$, $NR_7SO_2R_8$, and $SO_2NR_7R_8$;

$R_5$, $R_6$, $R_7$, and $R_8$ are independently selected from hydrogen, alkyl, substituted alkyl, and phenyl, or when attached to the same nitrogen atom (as in $NR_5R_6$ or $NR_7R_8$) may join together to form a heterocycle or heteroaryl; and m, n and q are independently 0, 1, or 2.

2. The compound of claim 1, or a pharmaceutically-acceptable salt thereof, in which X is $NR_1$ or $CR_1$, and $R_1$ is hydrogen, lower alkyl, or trifluoromethyl.

3. The compound of claim 1, or a pharmaceutically-acceptable salt thereof, in which X, $Y_1$ and $Y_2$ are selected so that ring A defines one of:

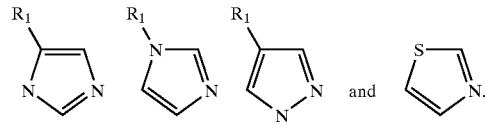

4. The compound of claim 1 or a pharmaceutically-acceptable salt thereof, in which:

$R_2$ is $C_{1-4}$alkyl optionally substituted with $OR_9$ or $NR_{10}R_{11}$;

$R_9$ is hydrogen or lower alkyl; and $R_{10}$ and $R_{11}$ are (i) independently selected from hydrogen, $C_{1-4}$alkyl, $C_{1-4}$substituted alkyl, and —(C=O)$C_{1-2}$alkyl, or alternatively (ii) together form a five to six membered heterocycle or heteroaryl.

5. The compound of claim 1, or a pharmaceutically-acceptable salt thereof, in which $R_2$ is $C_{1-2}$ alkyl optionally substituted with one of:

OH, $NH_2$, NH($C_{1-2}$alkyl), N($C_{1-2}$alkyl)$_2$, NH($C_{1-2}$ substituted alkyl), N($C_{1-2}$substituted alkyl)$_2$, NH(C=O)$C_{1-2}$ alkyl, or piperidinyl.

6. The compound of claim 1 or a pharmaceutically-acceptable salt thereof, in which $R_2$ is aryl having zero to three substituents selected from halogen, lower alkyl, trifluoromethyl, alkoxy, and nitro.

7. The compound of claim 1 or a pharmaceutically-acceptable salt thereof, in which
X, $Y_1$ and $Y_2$ are selected so that ring A defines one of pyrazolyl, imidazolyl, or thiazolyl;
$R_1$ is hydrogen, methyl, ethyl, or trifluoromethyl; and
$R_2$ is $C_{1-2}$alkyl optionally substituted with one of OH, $NH_2$, $NH(C_{1-2}alkyl)$, $N(C_{1-2}alkyl)_2$, $NH(C=O)C_{1-2}$ alkyl, or a five to six membered heterocycle.

8. The compound of claim 1, or a pharmaceutically-acceptable salt thereof, in which $R_3$ and $R_4$ are selected from halogen, alkyl, substituted alkyl, nitro, cyano, $OR_7$, $NR_7R_8$, $C(=O)R_7$, $CO_2R_7$, $SR_7$, $C(=O)NR_7R_8$, $NR_7C(=O)R_8$, $NR_7C(=O)OR_8$, $S(O)_qR_7$, $NR_7SO_2R_8$, and $SO_2NR_7R_8$;
$R_7$ and $R_8$ are independently selected from hydrogen and alkyl; and
m and n are independently 0, 1, or 2, provided that m and n are not both 0.

9. The compound of claim 1, or a pharmaceutically-acceptable salt thereof, in which m and n are both 0.

10. A compound having the formula,

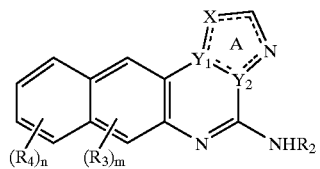

or a pharmaceutically-acceptable salt thereof, wherein
X is $NR_1$, $CR_1$, or S;
$Y_1$ and $Y_2$ are nitrogen or carbon, provided that:
a) when X is $CR_1$, at least one of $Y_1$ and $Y_2$ is nitrogen, and b) when one of $Y_1$ and $Y_2$ is carbon, the other of $Y_1$ and $Y_2$ is nitrogen and/or X is $NR_1$ or S, so that ring A defines a five-membered heteroaryl ring having at least two heteroatoms;
$R_1$ is hydrogen, halogen, lower alkyl, or trifluoromethyl;
$R_2$ is $C_{1-4}$ alkyl optionally substituted with a group selected from hydroxy, alkoxy, $NH_2$, NH(alkyl), $N(alkyl)_2$, NH(substituted alkyl), N(substituted alkyl)$_2$, and NH(C=O)alkyl, and heterocycle;
$R_3$ and $R_4$ are independently halogen, lower alkyl, substituted lower alkyl, nitro, cyano, alkoxy, amino, —$CO_2H$, —C(=O)H, or alkylthio; and
m and n are independently 0, 1, or 2.

11. The compound of claim 10, or a pharmaceutically-acceptable salt thereof, in which X, $Y_1$ and $Y_2$ are selected so that ring A defines one of:

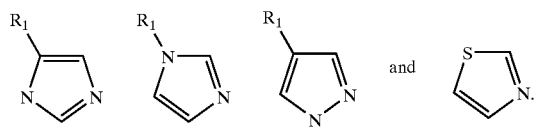

12. The compound of claim 11, or a pharmaceutically-acceptable salt thereof, in which:
$R_2$ is $C_{1-2}$ alkyl optionally substituted with a group selected from OH, $NH_2$, $NH(C_{1-2}alkyl)$, $N(C_{1-2}alkyl)_2$, $NH(C_{1-2}$substituted alkyl), $N(C_{1-2}$substituted alkyl)$_2$, and piperidinyl.

13. The compound of claim 1, selected from (i)
benzo[g]-4-(2-N-methylaminoethylamino)-1-methylimidazo[1,2-a]quinoxaline;
benzo[g]-4-methylamino-1-methylimidazo[1,2-a]quinoxaline;
benzo[g]-4-(2-N-methylaminoethylamino)-1-methylpyrazolo[1,2-a]quinazoline;
benzo[g]-4-methylamino-1-methylpyrazolo[1,2-a]quinazoline;
1-methyl-4-methylaminobenzo(g)-imidazo(4,5-c)quinoline;
1-methyl-4-(2-N-methylaminoethylamino)benzo(g)imidazo(4,5-c)quinoline,
1-methyl-4-methylaminobenzo(g)-thiazolo(4,5-c)quinoline;
1-methyl-4-(2-N-methylaminoethylamino)benzo(g)thiazolo(4,5-c)quinoline;
1-Methyl-4-(2-hydroxyethylamino)benzo[g]imidazo[1,2-a]quinoxaline,
1-Methyl-4-(2-piperidin-1-yl-ethylamino)benzo[g]imidazo[1,2-a]quinoxaline; and (ii) a pharmaceutically-acceptable salt thereof.

14. A pharmaceutical composition comprising (a) at least one compound according to claim 1, or a pharmaceutically acceptable salt thereof, and (b) a pharmaceutically acceptable carrier or diluent.

15. A pharmaceutical composition comprising (a) at least one compound according to claim 10, or a pharmaceutically acceptable salt thereof, and (b) a pharmaceutically acceptable carrier or diluent.

* * * * *

UNITED STATES PATENT AND TRADEMARK OFFICE
CERTIFICATE OF CORRECTION

PATENT NO. : 6,960,585 B2
APPLICATION NO. : 09/965977
DATED : November 1, 2005
INVENTOR(S) : Beaulieu et al.

It is certified that error appears in the above-identified patent and that said Letters Patent is hereby corrected as shown below:

In column 36, Line 28 "$R_7$, $CO_2R_7$, $SR_7$, $C(=O)NR_7R_8$, $NR_7C(=O)_8$, $NR_7C$" should read:

-- $R_7$, $CO_2R_7$, $SR_7$, $C(=O)NR_7R_8$, $NR_7C(=O)R_8$, $NR_7C$ --

In column 36, Line 52 "$R_2$ is $C_1$ $_4$alkyl optionally substituted with $OR_9$ or" should read:

-- $R_2$ is $C_{1-4}$alkyl optionally substituted with $OR_9$ or --

Signed and Sealed this

Nineteenth Day of June, 2007

JON W. DUDAS
*Director of the United States Patent and Trademark Office*